US010614966B2

United States Patent
Gangopadhyay et al.

(10) Patent No.: US 10,614,966 B2
(45) Date of Patent: Apr. 7, 2020

(54) ALIGNED GRAPHENE-CARBON NANOTUBE POROUS CARBON COMPOSITE

(71) Applicant: ARIZONA BOARD OF REGENTS ON BEHALF OF THE UNIVERSITY OF ARIZONA, Tucson, AZ (US)

(72) Inventors: Palash Gangopadhyay, Tucson, AZ (US); Scott H. Tan, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 301 days.

(21) Appl. No.: 15/502,480

(22) PCT Filed: Aug. 11, 2015

(86) PCT No.: PCT/US2015/044733
§ 371 (c)(1),
(2) Date: Feb. 7, 2017

(87) PCT Pub. No.: WO2016/025532
PCT Pub. Date: Feb. 18, 2016

(65) Prior Publication Data
US 2017/0221645 A1     Aug. 3, 2017

Related U.S. Application Data

(60) Provisional application No. 62/035,644, filed on Aug. 11, 2014.

(51) Int. Cl.
*H01G 11/38*     (2013.01)
*H01M 4/587*     (2010.01)
(Continued)

(52) U.S. Cl.
CPC ........... *H01G 11/38* (2013.01); *A61B 5/1468* (2013.01); *A61B 5/14532* (2013.01);
(Continued)

(58) Field of Classification Search
CPC ........ H01G 11/24; H01G 11/32; H01G 11/86; H01G 11/58; H01G 11/38; H01G 11/26;
(Continued)

(56) References Cited

U.S. PATENT DOCUMENTS 4,466,932 A * 8/1984 Koyama ............... C04B 35/524
                                                    264/29.3
5,990,041 A * 11/1999 Chung ..................... D01F 9/12
                                                    423/447.6
(Continued)

FOREIGN PATENT DOCUMENTS

CN       102049890 A       5/2011
WO    WO 2003/069019 A1    8/2003
(Continued)

OTHER PUBLICATIONS

Dimitrakakis et al. (2008) "Pillared Graphene: A New 3-D Network Nanostructure for Enhanced Hydrogen Storage," Nano Letters. 8(10):3166-70.
(Continued)

*Primary Examiner* — Golam Mowla
(74) *Attorney, Agent, or Firm* — Leydig, Voit & Mayer, Ltd.

(57) ABSTRACT

Embodiments of the present disclosure are directed to carbon-containing composites which are suitable for use as electrodes in electrochemical systems. The composites are formed from a scaffold of graphene and carbon nanotubes. Graphene flakes form a plurality of generally planar sheets (e.g., extending in an x-y plane) separated in the direction of a composite axis (e.g., along a z-axis) and approximately parallel to one another. The carbon nanotubes extend between the graphene sheets and at least a portion of the carbon nanotubes are aligned in approximately the same direction, at a defined angle with respect to the composite axis. At least a portion of the scaffold is embedded within a
(Continued)

CARBON NANOTUBES

GRAPHENE SHEETS porous carbon matrix (e.g., an activated carbon, a polymer derived graphitic carbon, etc.).

26 Claims, 35 Drawing Sheets

(51) Int. Cl.

| | | |
|---|---|---|
| H01G 11/24 | (2013.01) | |
| H01G 11/36 | (2013.01) | |
| A61B 5/145 | (2006.01) | |
| A61B 5/1468 | (2006.01) | |
| H01M 4/583 | (2010.01) | |
| H01G 11/32 | (2013.01) | |
| H01M 4/36 | (2006.01) | |
| C01B 32/15 | (2017.01) | |
| C01B 32/168 | (2017.01) | |
| C01B 32/194 | (2017.01) | |
| G01N 27/30 | (2006.01) | |
| H01G 11/26 | (2013.01) | |
| H01G 11/58 | (2013.01) | |
| H01G 11/86 | (2013.01) | |
| H01M 4/485 | (2010.01) | |
| H01M 4/58 | (2010.01) | |
| H01M 10/0525 | (2010.01) | |
| H01M 4/1393 | (2010.01) | |
| H01M 4/133 | (2010.01) | |
| B82Y 30/00 | (2011.01) | |
| B82Y 40/00 | (2011.01) | |

(52) U.S. Cl.
CPC ............ *C01B 32/15* (2017.08); *C01B 32/168* (2017.08); *C01B 32/194* (2017.08); *G01N 27/308* (2013.01); *H01G 11/24* (2013.01); *H01G 11/26* (2013.01); *H01G 11/32* (2013.01); *H01G 11/36* (2013.01); *H01G 11/58* (2013.01); *H01G 11/86* (2013.01); *H01M 4/362* (2013.01); *H01M 4/364* (2013.01); *H01M 4/485* (2013.01); *H01M 4/583* (2013.01); *H01M 4/587* (2013.01); *H01M 4/5825* (2013.01); *H01M 10/0525* (2013.01); *A61B 2562/0285* (2013.01); *A61B 2562/125* (2013.01); *B82Y 30/00* (2013.01); *B82Y 40/00* (2013.01); *C01B 2202/02* (2013.01); *C01B 2202/08* (2013.01); *C01B 2204/02* (2013.01); *C01B 2204/04* (2013.01); *H01M 4/133* (2013.01); *H01M 4/1393* (2013.01); *H01M 2300/0045* (2013.01); *Y02E 60/13* (2013.01); *Y10S 977/734* (2013.01); *Y10S 977/75* (2013.01); *Y10S 977/753* (2013.01); *Y10S 977/842* (2013.01); *Y10S 977/892* (2013.01); *Y10S 977/948* (2013.01)

(58) Field of Classification Search
CPC ...... H01G 11/36; H01M 4/583; H01M 4/133; H01M 4/1393; H01M 4/362; H01M 4/587; H01M 4/5825; H01M 4/485; H01M 4/364
See application file for complete search history.

(56) References Cited

U.S. PATENT DOCUMENTS

| | | | |
|---|---|---|---|
| 6,555,945 B1 | 4/2003 | Baughman et al. | |
| 6,630,772 B1 | 10/2003 | Bower et al. | |
| 6,723,396 B1 | 4/2004 | Patrick | |
| 6,824,974 B2 | 11/2004 | Pisharody et al. | |
| 6,936,228 B2 | 8/2005 | Hirakata et al. | |
| 6,969,690 B2 | 11/2005 | Zhou et al. | |
| 7,008,563 B2 | 3/2006 | Smalley et al. | |
| 7,018,261 B2 | 3/2006 | Perlo et al. | |
| 7,132,039 B2 | 11/2006 | Anazawa et al. | |
| 7,147,966 B2 | 12/2006 | Ren et al. | |
| 7,252,884 B2* | 8/2007 | Su .......................... B82Y 30/00 428/408 |
| 7,442,284 B2 | 10/2008 | Ren et al. | |
| 7,466,523 B1 | 12/2008 | Chen | |
| 7,508,039 B2 | 3/2009 | Al-Rabadi | |
| 7,723,180 B2 | 5/2010 | Chen et al. | |
| 7,735,147 B2 | 6/2010 | Jin et al. | |
| 7,758,921 B2 | 7/2010 | Liu et al. | |
| 7,764,534 B2 | 7/2010 | Thorp et al. | |
| 7,771,784 B2 | 8/2010 | Loutfy et al. | |
| 7,803,262 B2 | 9/2010 | Haik et al. | |
| 7,819,633 B2 | 10/2010 | Qian et al. | |
| 7,830,698 B2 | 11/2010 | Chen et al. | |
| 7,833,355 B2 | 11/2010 | Capizzo | |
| 7,846,819 B2 | 12/2010 | Pribat et al. | |
| 7,875,801 B2 | 1/2011 | Tsotsis | |
| 7,875,802 B2 | 1/2011 | Tsotsis | |
| 7,916,838 B2 | 3/2011 | Perkins et al. | |
| 7,923,812 B2 | 4/2011 | Scheuerlein | |
| 7,947,976 B2 | 5/2011 | Merkulov et al. | |
| 8,007,871 B2 | 8/2011 | Man et al. | |
| 8,008,213 B2 | 8/2011 | Xiao et al. | |
| 8,014,185 B2 | 9/2011 | Scheuerlein | |
| 8,019,097 B2 | 9/2011 | Jiang et al. | |
| 8,023,310 B2 | 9/2011 | Fu et al. | |
| 8,073,165 B2 | 12/2011 | Jiang et al. | |
| 8,084,366 B2 | 12/2011 | Chan et al. | |
| 8,137,858 B2 | 3/2012 | Liu et al. | |
| 8,203,864 B2 | 6/2012 | Herner et al. | |
| 8,241,522 B2 | 8/2012 | Li | |
| 8,421,050 B2 | 4/2013 | Ping et al. | |
| 8,450,835 B2 | 5/2013 | Chen et al. | |
| 8,537,640 B2 | 9/2013 | Jiang et al. | |
| 8,551,376 B2 | 10/2013 | Lemaire et al. | |
| 8,580,104 B2 | 11/2013 | Unwin et al. | |
| 8,614,466 B2 | 12/2013 | Rasooly et al. | |
| 8,710,481 B2 | 4/2014 | Kai et al. | |
| 8,748,504 B2 | 6/2014 | Elimelech et al. | |
| 8,748,871 B2 | 6/2014 | Avouris et al. | |
| 9,327,472 B1* | 5/2016 | Zehavi .................. B01D 39/20 |
| 2002/0011443 A1* | 1/2002 | Komatsu ............... B01D 63/024 210/650 |
| 2002/0192141 A1 | 12/2002 | Little | |
| 2004/0184981 A1 | 9/2004 | Liu et al. | |
| 2006/0115640 A1 | 6/2006 | Yodh et al. | |
| 2006/0276056 A1 | 12/2006 | Ward et al. | |
| 2007/0059233 A1* | 3/2007 | Sheem ................... B01J 20/20 423/445 R |
| 2007/0120095 A1 | 5/2007 | Gruner | |
| 2007/0122687 A1* | 5/2007 | Sakurai ............. B01D 39/1653 442/59 |
| 2007/0153363 A1 | 7/2007 | Gruner | |
| 2009/0095412 A1 | 4/2009 | Abrams et al. | |
| 2010/0190639 A1* | 7/2010 | Worsley ................. B01J 21/063 502/183 |
| 2011/0096465 A1 | 4/2011 | Zhou et al. | |
| 2011/0204020 A1 | 8/2011 | Ray et al. | |
| 2012/0026643 A1 | 2/2012 | Yu et al. | |
| 2012/0077006 A1* | 3/2012 | Worsley .................. C04B 35/83 428/219 |
| 2012/0103510 A1 | 5/2012 | Wang et al. | |
| 2013/0000961 A1 | 1/2013 | Strachan et al. | |
| 2013/0141050 A1 | 6/2013 | Visco et al. | |
| 2013/0230751 A1 | 9/2013 | Shaw et al. | |
| 2013/0295374 A1* | 11/2013 | Tang ...................... B82B 1/002 428/323 |
| 2014/0029161 A1 | 1/2014 | Beidaghi et al. | |

FOREIGN PATENT DOCUMENTS

| | | | |
|---|---|---|---|
| WO | WO 2004/043857 A2 | 5/2004 | |
| WO | WO 2004/065294 A2 | 8/2004 | |

(56) References Cited

FOREIGN PATENT DOCUMENTS

| WO | WO 2005/014259 A1 | 2/2005 |
|---|---|---|
| WO | WO 2005/031299 A2 | 4/2005 |
| WO | WO 2005/074404 A2 | 8/2005 |
| WO | WO 2005/103347 A2 | 11/2005 |
| WO | WO 2006/041691 A2 | 4/2006 |
| WO | WO 2006/080702 A1 | 8/2006 |
| WO | WO 2007/030484 A2 | 3/2007 |
| WO | WO 2007/061428 A2 | 5/2007 |
| WO | WO 2008/057615 A2 | 5/2008 |
| WO | WO 2009/058855 A2 | 5/2009 |
| WO | WO 2010/059505 A1 | 5/2010 |
| WO | WO 2011/112598 A1 | 9/2011 |
| WO | WO 2011/163129 A2 | 12/2011 |
| WO | WO 2012/059716 A1 | 5/2012 |
| WO | WO 2012/142269 A1 | 10/2012 |
| WO | WO 2012/151027 A1 | 11/2012 |
| WO | WO 2013/119295 A1 | 8/2013 |
| WO | WO 2013/119295 A9 | 9/2013 |

OTHER PUBLICATIONS

Dimitrakakis et al. (Mar. 8, 2009) "Designing novel carbon nanostructures for hydrogen storage," SPIE Newsroom. Accessible on the Internet at URL: http://spie.org/newsroom/1451-designing-novel-carbon-nanostructures-for-hydrogen-storage?SSO=1, 2 pgs. [Last Accessed Feb. 1, 2018].

Du et al. (2011) "Preparation of Tunable 3D Pillared Carbon Nanotube—Graphene Networks for High-Performance Capacitance," Chem. Mater. 23:4810-4816.

Fan et al. (2010) "A Three-Dimensional Carbon Nanotube/Graphene Sandwich and Its Application as Electrode in Supercapacitors," Adv. Mater. 22:3723-8.

Han et al. (May 30, 2014) "Electrochemical Signal Amplification for Immunosensor Based on 3d Interdigitated Array Electrodes," Analytical Chemistry. 86:5991-5998.

Kulkarni et al. (Jan. 2, 2014) "High-Performance Supercapacitor Electrode Based on a Polyaniline Nanofibers/3D Graphene Framework as an Efficient Charge Transporter," Journal of Materials Chemistry A. 2:4989-4998.

Lian et al. (Aug. 15, 2014) "Design and Synthesis of Porous Nano-Sized Sn@C/Graphene Electrode Material with 3D Carbon Network for High-Performance Lithium-Ion Batteries," Journal of Alloys and Compounds. 604:188-195.

Oltean et al. (Apr. 8, 2014) "A Li-Ion Microbattery with 3d Electrodes of Different Geometries," ECS Electrochemistry Letters. 3:A54-A57.

Tan et al. (Aug. 11, 2014) "Fabrication of Three-Dimensional Gridlocked Hierarchical Nanostructured Carbon Electrodes using Graphene and Aligned Single-Walled Carbon Nanotubes; and their applications as Supercapacitor Electrodes," Poster Presentation, Undergraduate Research Opportunities Consortium, 2014, The University of Arizona.

Verma (Archived Webpage from Jan. 5, 2012) "Activated Carbon fibers in Environmental Applications," Indian Institute of Technology Kanpur. Accessible on the Internet at URL: https://web.archive.org/web/20120105090011/http://www.iitk.ac.in/infocell/iitk/newhtml/storyoftheweek52.htm, 4 pgs. [Last Accessed Feb. 1, 2018].

Wei et al. (Mar. 4, 2014) "3D Mesoporous Hybrid Nico2o4@Graphene Nanoarchitectures as Electrode Materials for Supercapacitors with Enhanced Performances," Journal of Materials Chemistry A. 2:8103-8109.

Wu et al. (May 2014) "3D Amorphous Carbon and Graphene Co-Modified Lifepo4 Composite Derived from Polyol Process as Electrode for High Power Lithium-Ion Batteries," Journal of Energy Chemistry. 23(3):363-375.

Xie et al. (Jun. 22, 2014) "Development of a 3d Graphene Electrode Dielectrophoretic Device," Journal of Visualized Experiments. 88:e51696. pp. 1-11.

Zhan et al. (May 6, 2014) "Free-Standing Electrochemical Electrode Based on Ni(Oh)(2)/3d Graphene Foam for Nonenzymatic Glucose Detection," Nanoscale. 6:7424-7429.

Zhi et al. (Nov. 27, 2013) "Highly Conductive Ordered Mesoporous Carbon Based Electrodes Decorated by 3D Graphene and 1D Silver Nanowire for Flexible Supercapacitor," Advanced Functional Materials. 24:2013-2019.

International Search Report with Written Opinion corresponding to International Patent Application No. PCT/US2015/044733, dated Nov. 9, 2015.

* cited by examiner

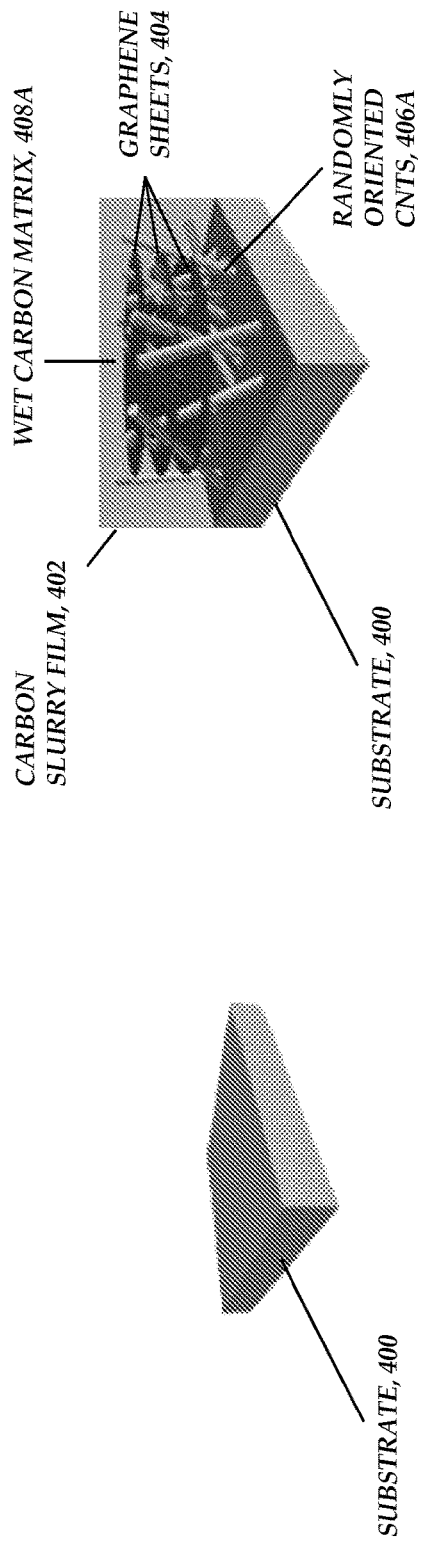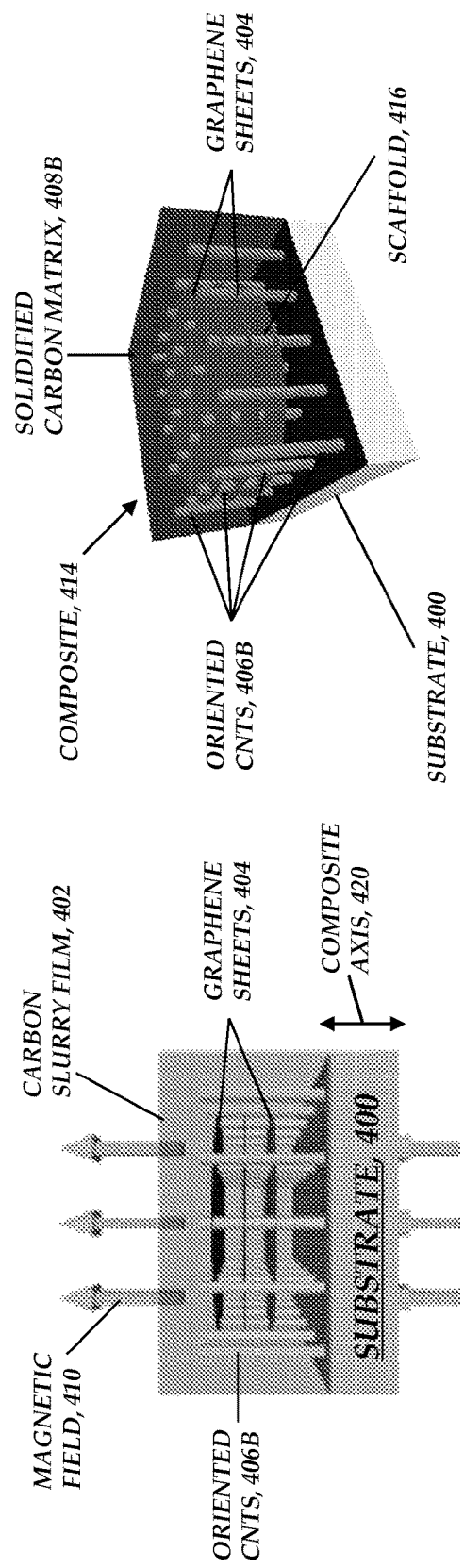

ALIGNED GRAPHENE-CARBON NANOTUBE POROUS CARBON COMPOSITE

CROSS-REFERENCE TO RELATED APPLICATIONS

This application is a U.S. National Stage Application under 35 U.S.C. § 371 of International Application No. PCT/US2015/044733, filed Aug. 11, 2015, which claims the benefit of U.S. Provisional Application No. 62/035,644, filed on Aug. 11, 2014, and entitled, "Aligned Graphene—Carbon Nanotube Embedded in Graphitic Amorphous Activated Carbon as Three Dimensional Carbon Electrodes." The entirety of the each of the above applications including its teachings is incorporated herein by reference.

GOVERNMENT SUPPORT

This invention was made with government support under Grant No. EEC1359163 awarded by NSF. The government has certain rights in the invention.

BACKGROUND

Effective and low-cost energy storage devices are the subject of extensive research efforts. Supercapacitors are one technology under consideration as an improved alternative to over typical rechargeable batteries.

There are two classes of supercapacitors, distinguished by their mechanism of operation. The first, referred to as electrochemical double layer capacitors (EDLCs), include two electrodes that are mechanically separated from one another while also electrically connected by an electrolyte (a mixture of positive and negative ions within a solvent). Applying potential between the positive and negative electrodes results in attraction of negative and positive ions to the positive and negative electrodes, respectively. As a result, an electrical double layer is generated at each electrode. The double layer includes two different charge layers, one formed in the surface of each electrode and the other charge layer formed from opposite polarity ions within the electrolyte. The two charge layers are separated by a layer of polarized solvent molecules, producing a static electric field within the solvent separation layer that stores electrical charge. The amount of charge stored per unit voltage within the supercapacitor is primarily a function of the electrode size. As no chemical change takes place within the electrode or electrolyte, the ability to charge and discharge the supercapacitor is theoretically unlimited. The second class of supercapacitors, referred to as pseudocapacitors or redox capacitors, stores charge electrochemically by electron charge transfer between the electrode and electrolyte. This charge storage is achieved by electroabsorption, reduction-oxidation (redox) reactions and intercalation. Of the two supercapacitor designs, EDLCs are preferred due to the absence of electrochemical reactions.

Supercapacitor electrodes are typically formed from porous materials. The porosity provides improved access to charges from the electrolyte, which in turn increases the effective electrochemical surface area of the electrode available for formation of the double layer. Porous carbon is typically employed as an electrode material due to its low cost, high specific surface area, and easily accessed ordered pore channels. However, porous carbon electrodes suffer from poor electrical conductivity and mechanical flexibility, as well as relatively low specific capacitance and cycling stability.

Recently, electrodes formed from graphene and carbon nanotubes have been proposed. However, these structures suffer from numerous limitations, including efficiency, structural integrity, electrical conductivity, reduced porosity, and limited ability to process in bulk.

Accordingly, there exists a continued need for improved electrodes for use in energy storage devices such as supercapacitors.

SUMMARY

Embodiments of the present disclosure are directed to carbon-containing composite systems which are suitable for use as electrodes. The composite systems are formed from a scaffold of graphene and carbon nanotubes at least partially embedded in a matrix of porous carbon (e.g., an activated carbon, a polymer derived graphitic carbon, etc.). Graphene flakes form a plurality of generally planar sheets (e.g., extending in an x-y plane) separated in the direction of a composite axis (e.g., along a z-axis) and approximately parallel to one another. The carbon nanotubes extend between the graphene sheets, where at least a portion of the carbon nanotubes are aligned in approximately the same direction, at a defined angle with respect to the composite axis. The composite is highly porous and, when utilized as electrode, exhibits an active surface area many times greater than that of existing electrodes, increasing performance of the composite electrode.

In an embodiment, a composite material is provided. The composite material includes a scaffold and a matrix. The scaffold includes a plurality of graphene sheets each oriented in an independent alignment plane substantially perpendicular to a composite axis an a plurality of carbon nanotubes, where at least a portion of the carbon nanotubes are oriented such that their respective tube axes are oriented substantially at a defined angle with respect to the composite axis. The matrix includes a porous carbon, wherein the scaffold is at least partially embedded in the matrix.

Embodiments of the composite material may further include one or more of the following, in any combination.

In an embodiment, the composite further includes at least two graphene sheets, where the plurality of carbon nanotubes extends between the at least two graphene sheets.

In an embodiment of the composite, the at least two graphene sheets are separated by a distance within the range between about 0.8 nm to about 2000 nm.

In an embodiment of the composite, the plurality of graphene sheets includes at least one of single layer graphene, multi-layer graphene, and reduced graphene oxide (RGO).

In an embodiment of the composite, a mean diameter of each of the plurality of graphene sheets is within the range between about 50 nm to about 75 µm.

In an embodiment of the composite, the plurality of carbon nanotubes includes at least one of metallic carbon nanotubes and semiconducting carbon nanotubes.

In an embodiment of the composite, the plurality of carbon nanotubes are single-walled carbon nanotubes.

In an embodiment of the composite, a mean outer diameter of the plurality of carbon nanotubes is within the range between about 0.8 nm to about 2 nm.

In an embodiment of the composite, a mean length of the plurality of carbon nanotubes is within the range between about 2 nm to about 20 nm.

In an embodiment of the composite, the plurality of carbon nanotubes are functionalized with one or more functional groups selected from the group consisting of carboxylic acid (—COOH), sulphonic acid (—SO$_3$H), amine (—NH$_2$), and hydroxyl (—OH) containing groups.

In an embodiment of the composite, the tube axes of approximately all of the carbon nanotubes are oriented approximately parallel to the composite axis.

In an embodiment of the composite, a thickness of the composite is within the range between about 20 µm to about 500 µm.

In an embodiment, the composite further includes a binder, where the porous carbon is an activated carbon and where the binder connects at least a portion of the plurality of graphene sheets to at least a portion of the plurality of carbon nanotubes via the porous carbon matrix.

In an embodiment of the composite, the binder is selected from the group consisting of polyvinylidene fluoride (PVDF), polyacrylonitrile (PAN), polytetrafluoroethylene (PTFE), carboxymethylcellulose (CMC), polystyrene, styrene-butadiene rubber (SBR), poly(ethylene oxide), functionalized graphene oxide, and silver paste.

In an embodiment of the composite, the porous carbon is formed from one of carbonized polyacrylonitrile (PAN) and polystyrene.

In an embodiment of the composite, the plurality of graphene sheets and the plurality of carbon nanotubes are not connected to each other by chemical bonding.

In an embodiment of the composite, the plurality of graphene sheets and the plurality of carbon nanotubes are mechanically connected to one another.

In an embodiment of the composite, the plurality of graphene sheets and the plurality of carbon nanotubes are connected to one another by adhesion.

In an embodiment of the composite, the porous matrix further comprises an interconnected pore network, extending from an outer surface of the composite to the embedded scaffold.

In an embodiment of the composite, a mean diameter of the pores of the pore network decreases with distance from the outer surface of the composite.

In an embodiment of the composite, the pore network includes a macroporous region positioned adjacent the outer surface of the composite and wherein the mean diameter of the pores is greater than 50 nm within the macroporous region.

In an embodiment of the composite, the pore network includes a mesoporous region positioned inward of, and interconnected with, the macroporous region and wherein the mean diameter of the pores is within the range between less than 50 nm and greater than 2 nm within the mesoporous region.

In an embodiment of the composite, the pore network includes a microporous region positioned inward of, and interconnected with, the mesoporous region and wherein the mean diameter of the pores is within the range between less than 2 nm within the microporous region.

In an embodiment of the composite, a specific surface area of the composite is within the range between about 700 m$^2$/g to about 2500 m$^2$/g.

In an embodiment of the composite, the composite includes: about 0.1% to about 5% carbon nanotubes; about 0.1% to about 5% graphene; about 70% to about 98.8% porous carbon; and about 1% to about 20% binder on the basis of the total weight of the composite.

In an embodiment of the composite, the composite includes: about 0.1% to about 5% carbon nanotubes; about 0.1% to about 5% graphene; and about 90% to about 99.8% porous carbon on the basis of the total weight of the composite.

In an embodiment of the disclosure, a composite electrode is provided. The composite includes a scaffold and a matrix. The scaffold includes a plurality of graphene sheets each oriented in an independently alignment plane substantially perpendicular to a composite axis; and a plurality of carbon nanotubes, wherein at least a portion of the carbon nanotubes are oriented such that their respective tube axes are oriented substantially at a defined angle with respect to the composite axis. The matrix includes a porous carbon, where the scaffold is at least partially embedded in the matrix.

In an embodiment of the disclosure, an electrochemical system is provided. The electrochemical system includes a first electrode and a second electrode, wherein at least one of the first electrode and the second electrode is a composite material. The composite material includes a scaffold and a matrix. The scaffold includes a plurality of graphene sheets each oriented in an independent alignment plane substantially perpendicular to a composite axis and a plurality of carbon nanotubes, where at least a portion of the carbon nanotubes are oriented such that their respective tube axes are oriented substantially at a defined angle with respect to the composite axis. The matrix includes a porous carbon, where the scaffold is at least partially embedded in the matrix. The electrochemical system further includes an electrolyte provided between the two electrodes and a separator mechanically separating the two electrodes.

Embodiments of the electrochemical system may include one or more of the following, in any combination.

In an embodiment of the electrochemical system, at least one composite electrode is mounted upon a supporting substrate.

In an embodiment of the electrochemical system, the substrate includes one of carbon coated copper, a flexible graphite film, carbon coated aluminum, and nickel.

In an embodiment of the electrochemical system, the at least one composite electrode is free standing.

In an embodiment of the electrochemical system, the separator is an ion-permeable membrane.

In an embodiment of the electrochemical system, the ion-permeable membrane comprises one of a semi-permeable filter paper, a semi-permeable glass-fiber filter, and a semi-permeable polymer filter.

In an embodiment of the electrochemical system, the ion-permeable membrane possesses a mean pore size within the range between about 0.05 µm to about 50 µm.

In an embodiment of the electrochemical system, the electrolyte is a room-temperature ionic liquid.

In an embodiment of the electrochemical system, the electrolyte is selected from the group consisting of: potassium hydroxide (KOH), sulfuric acid (H$_2$SO$_4$), 1-butyl-4-methylpyridinium tetrafluoroborate (4MBPBF$_4$), 1-ethyl-3-methylimidazolium trifluoromethanesulfonate (EMIM-OTf), 1-ethyl-3-methylimidazolium tetrafluoroborate (EMIMBF$_4$), sodium sulfate (Na$_2$SO$_4$), 1-butyl-2,3-dimethylimidazolium bis(trifluoromethylsuphonyl)imide (EMIM-TFSI), N-butyl-N-methylpyrrolidinium bis(trifluoromethanesulfonyl)imide (PYR$_{14}$-TFSI), and 1-ethyl-3-methylimidazolium bis(trifluoromethane-sulfonyl)azanide (EMIM-TFSA).

In an embodiment of the electrochemical system, the electrolyte is not an organic electrolyte.

In an embodiment of the electrochemical system, the electrolyte is a solid electrolyte.

In an embodiment of the electrochemical system, the electrode further includes a lithium compound embedded within the composite.

In an embodiment of the electrochemical system, the lithium compound is selected from the group consisting of: lithium titanate ($LiTi_5O_{12}$) and lithium metal-orthosilicates ($LiMSiO_4$) where M is iron (Fe), manganese (Mn), or nickel (Ni).

In an embodiment of the electrochemical system, the at least one electrode includes: about 0.1% to about 5% carbon nanotubes; about 0.1% to about 5% graphene; up to about 2% porous carbon; and about 88% to about 99.8% lithium compound on the basis of the total weight of the electrode.

Embodiments of the electrochemical device may further include about 0.1% to about 2% binder.

In an embodiment of the disclosure, the electrochemical device is a supercapacitor.

In an embodiment of the disclosure, the electrochemical device is a primary battery.

In an embodiment of the disclosure, the electrochemical device is a secondary battery.

In an embodiment of the disclosure, the electrochemical device is a primary fuel cell.

In an embodiment of the disclosure, a method for fabricating a composite material is provided. The method includes providing a carbon slurry. The carbon slurry includes a first solvent; a porous carbon; a plurality of conductive graphene sheets; and a plurality of carbon nanotubes. Embodiments of the method further include depositing a film of the carbon slurry upon a substrate; positioning the carbon slurry film within a magnetic field and sonic wave, where the magnetic field lines are oriented at a defined angle with respect to the plane of the substrate and where the magnetic field strength is sufficient to induce at least a portion of the carbon nanotubes to orient such that their respective tube axes are substantially parallel to the magnetic field lines; and removing at least a portion of the solvents from the deposited film to form a solidified film of the composite.

Embodiments of the method may include one or more of the following, in any combination.

In an embodiment of the method, after removing the solvents: the plurality of graphene sheets and the plurality of carbon nanotubes form a three-dimensional scaffold embedded within a matrix formed by the porous carbon, the plurality of graphene sheets and the plurality of carbon nanotubes are connected to each other via the porous carbon matrix; the plurality of graphene sheets are oriented approximately parallel to the substrate; and the plurality of carbon nanotubes maintains the orientation of their respective tube axes at the defined angle with respect to the plane of the substrate.

In an embodiment of the method, the carbon slurry further includes a binder and providing the carbon slurry further includes: mixing the porous carbon and the binder with the first solvent to form a first slurry precursor; sonicating the first slurry precursor; mixing the sonicated first slurry precursor with a dispersion of the plurality of graphene sheets in a second solvent to form a second slurry precursor, where the first and second solvents are miscible; sonicating the second slurry precursor; mixing the sonicated second slurry precursor with a dispersion of the plurality of carbon nanotubes in the first solvent to form the carbon slurry; and sonicating the carbon slurry.

In an embodiment of the method, the carbon slurry further includes a binder and the porous carbon is an activated carbon and wherein the binder connects the plurality of graphene sheets to the plurality of carbon nanotubes via the porous carbon matrix.

In an embodiment of the method, the binder is selected from the group consisting of polyvinylidene fluoride (PVDF), polyacrylonitrile (PAN), carboxymethylcellulose (CMC), polystyrene, styrene-butadiene rubber (SBR), poly (ethylene oxide), functionalized graphene oxide, and silver paste.

In an embodiment of the method, a BET surface area of the activated carbon is within the range between about 700 to about 2500 $m^2/g$ In an embodiment of the method, the composite includes: about 0.1% to about 0.5% carbon nanotubes; about 1% to about 5% graphene; about 80% to about 85% porous carbon; and about 10% to about 20% binder on the basis of the total weight of the composite.

In an embodiment of the method, the porous carbon is formed from a polymer precursor resin and providing the carbon slurry further includes:

mixing the polymer precursor with the first solvent to form a first slurry precursor; sonicating the first slurry precursor; mixing the sonicated first slurry precursor with a dispersion of the plurality of graphene sheets in a second solvent to form a second slurry precursor, where the first and second solvents are miscible; sonicating the second slurry precursor; mixing the sonicated second slurry precursor with a dispersion of the plurality of carbon nanotubes in the first solvent to form the carbon slurry; and sonicating the carbon slurry.

Embodiments of the method further include heating the solidified composite film to carbonize the polymer precursor and form the porous carbon.

In an embodiment of the method, the polymer precursor is selected from the group consisting of polyacrylonitrile (PAN) and polystyrene.

In an embodiment of the method, a maximum diameter of the polymer precursor is less than or equal to about 45 µm.

In an embodiment of the method, the plurality of graphene sheets and the plurality of carbon nanotubes are not connected to each other by chemical bonding.

Embodiments of the method further include comprising removing the solidified composite film from the substrate to form a free-standing composite film.

In an embodiment of the method, the magnetic field strength is within the range between about 0.3 T to about 3 T.

In an embodiment of the method, the first solvent is selected from the group consisting of: dimethylformamide (DMF) or N-methyl pyrrolidone (NMP) and the second solvent is selected from the group consisting of: N-butyl acetate, acetone, or diethylketone.

In an embodiment of the method, the composite includes at least two graphene sheets, where the plurality of carbon nanotubes extends between the at least two graphene sheets.

In an embodiment of the method, the at least two graphene sheets are separated by a distance within the range between about 0.8 nm to about 2000 nm.

In an embodiment of the method, the plurality of graphene sheets comprises at least one of single layer graphene, multi-layer graphene, and reduced graphene oxide (RGO).

In an embodiment of the method, a mean diameter of each of the plurality of graphene sheets is within the range between about 50 nm to about 75 µm.

In an embodiment of the method, the plurality of carbon nanotubes comprise at least one of metallic carbon nanotubes and semiconducting carbon nanotubes.

In an embodiment of the method, the plurality of carbon nanotubes are single-walled carbon nanotubes.

In an embodiment of the method, a mean outer diameter of the plurality of carbon nanotubes is within the range between about 0.8 nm to about 2 nm.

In an embodiment of the method, a mean length of the plurality of carbon nanotubes is within the range between about 2 nm to about 10 nm.

In an embodiment of the method, the plurality of carbon nanotubes are functionalized with one or more functional groups selected from the group consisting of carboxylic acid (—COOH), sulphonic acid (—SO$_3$H), amine (—NH$_2$), and hydroxyl (—OH) containing groups.

In an embodiment of the method, the tube axes of approximately all of the carbon nanotubes are oriented at approximately 90 degrees to the plurality of graphene sheets.

In an embodiment of the method, a thickness of the composite is within the range between about 20 μm to about 500 μm.

In an embodiment of the method, the porous matrix further comprises an interconnected pore network, extending from an outer surface of the composite to the embedded scaffold.

In an embodiment of the method, a mean diameter of the pores of the pore network decreases with distance from the outer surface of the composite.

In an embodiment of the method, the pore network comprises a macroporous region positioned adjacent the outer surface of the composite and wherein the mean diameter of the pores is greater than 50 nm within the macroporous region.

In an embodiment of the method, the pore network comprises a mesoporous region positioned inward of, and interconnected with, the macroporous region and wherein the mean diameter of the pores is within the range between less than 50 nm and greater than 2 nm within the mesoporous region.

In an embodiment of the method, the pore network comprises a microporous region positioned inward of, and interconnected with, the mesoporous region and wherein the mean diameter of the pores is within the range between less than 2 nm within the microporous region.

In an embodiment of the method, a specific surface area of the composite is within the range between about 700 m$^2$/g to about 2500 m$^2$/g.

In an embodiment of the method, the carbon slurry film is positioned within the magnetic field while the film is viscous.

In an embodiment of the method, at least a portion of the solvents are removed from the deposited film while the deposited film is positioned within the magnetic field.

In an embodiment of the method, the sonic wave includes a pulsed sonic wave having a power of about 700 W at a frequency of about 20 kHz for a duration within the range between about 20 minutes to about 6 hours.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

FIGS. 4A-4D are schematic illustrations depicting fabrication of an embodiment of a composite film of the present disclosure;

Figure 15A:
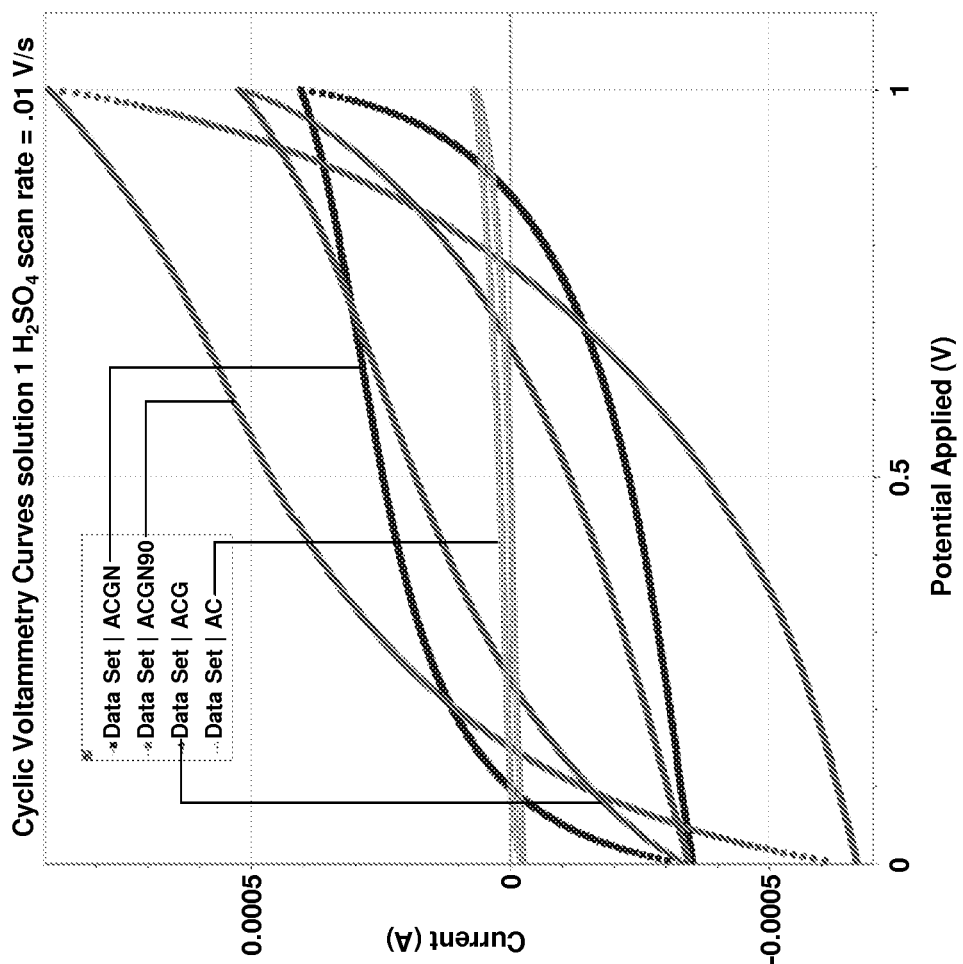
Figure 15B:
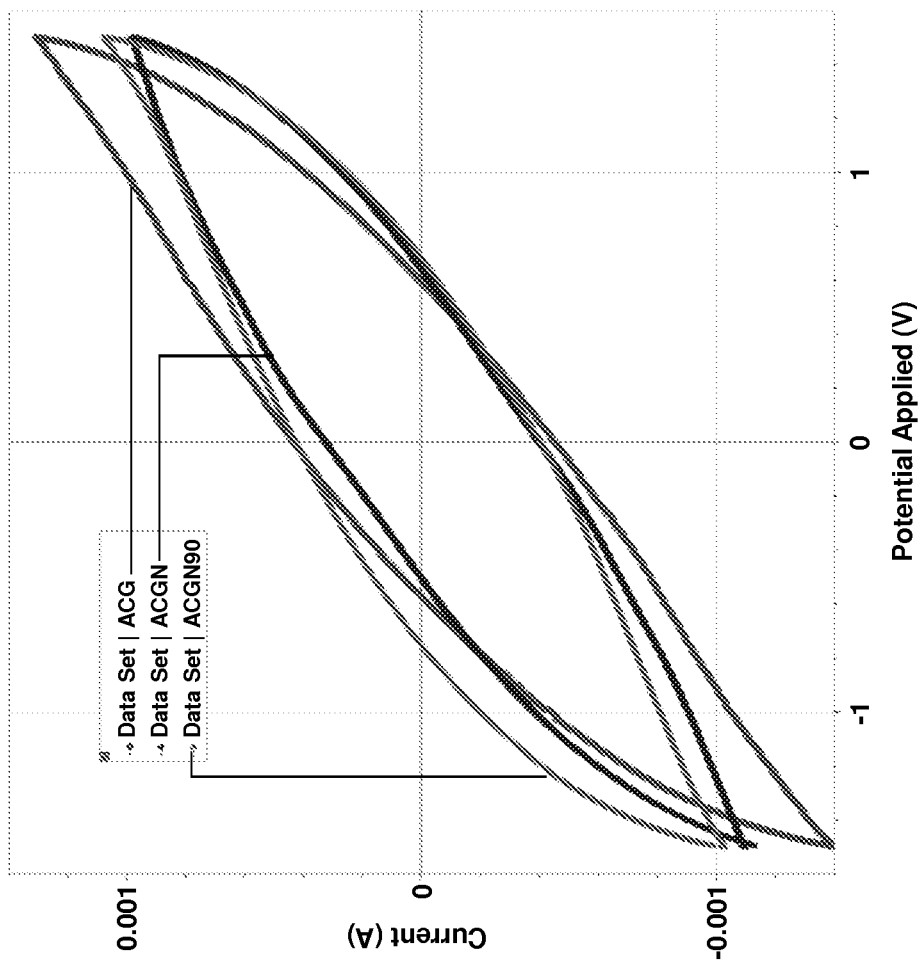
Figure 15C:
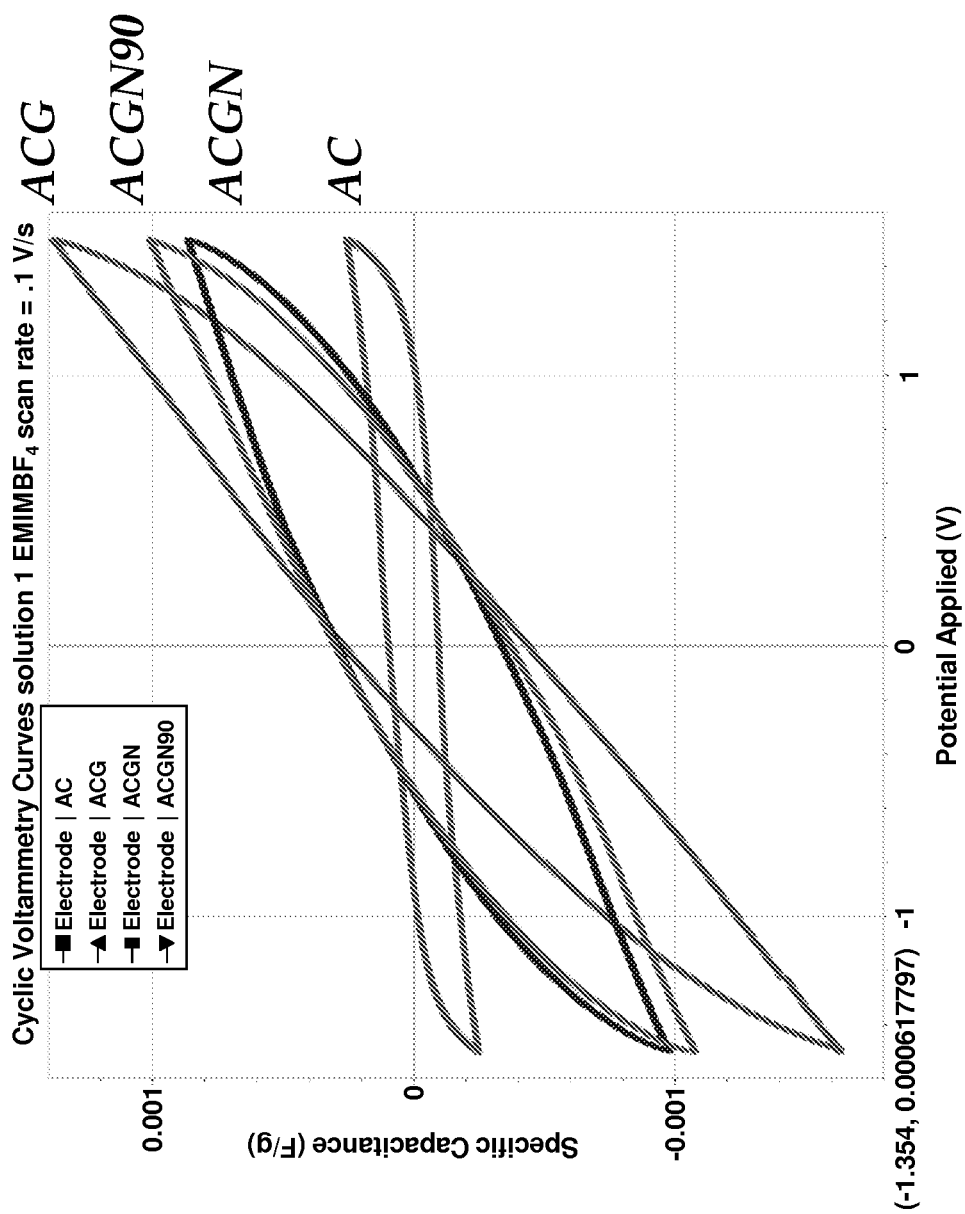
Figure 16A:
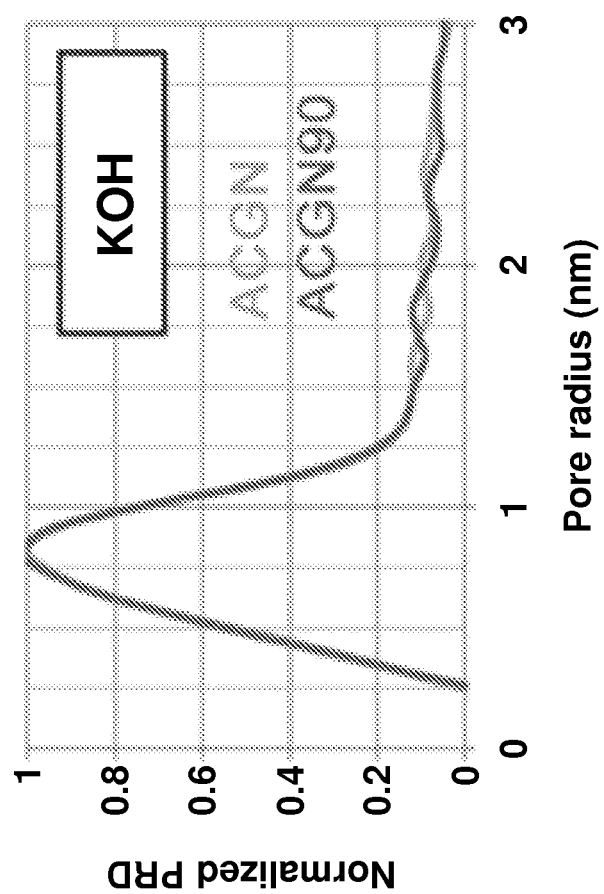
Figure 16B:
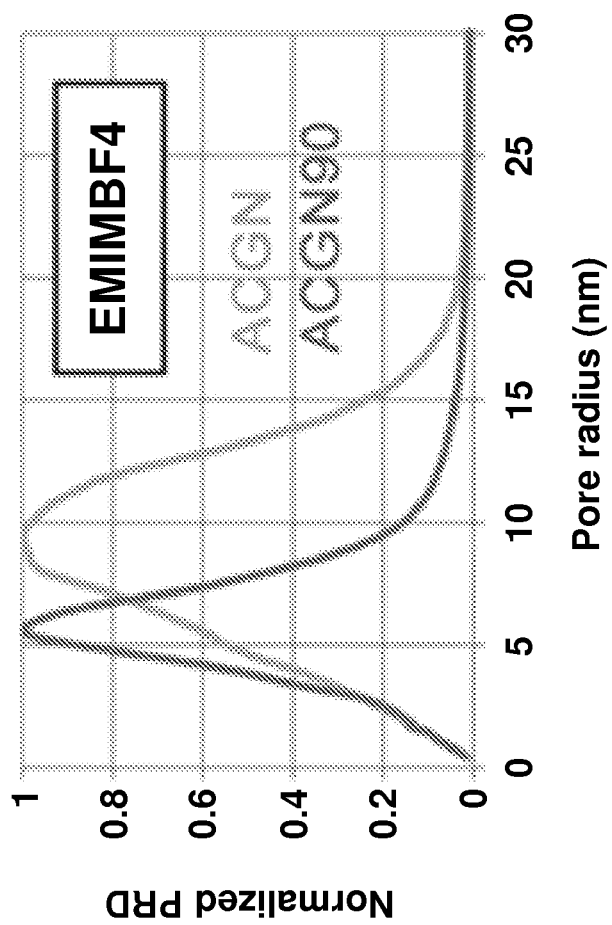
Figure 16C:
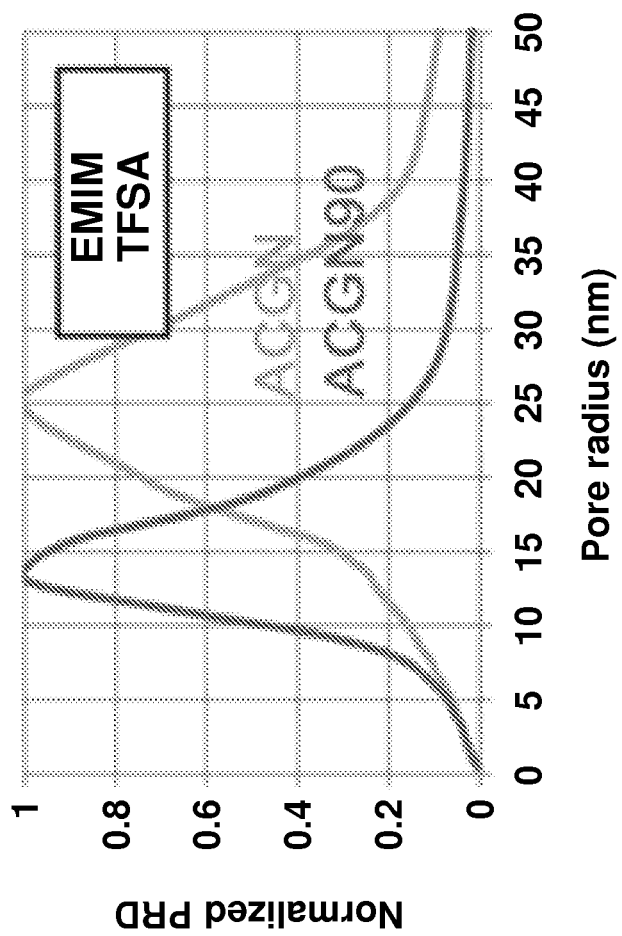

FIGS. 15A-15C are plots of CV measurements on embodiments of supercapacitors composed of AC, ACG, ACGN, and ACGN90 electrodes on carbon coated copper substrates and a paper separator with electrolytes of H$_2$SO$_4$, EMIMTFSi, and EMIMBF$_4$, respectively; and FIGS. 16A-16C present experimental measurements of normalized pore size distribution as a function of pore radius for embodiments of supercapacitors composed of ACGN and ACGN90 on carbon coated copper foils and a paper separator with of the present disclosure.

DETAILED DESCRIPTION

In general, the terms and phrases used herein have their art-recognized meaning, which can be found by reference to standard texts, journal references and contexts known to those skilled in the art. The following definitions are provided to clarify their specific use in the context of the disclosed embodiments.

"Material property" refers to the response of a material to an external stimulus. Non-limiting examples of material properties include mechanical properties, electrical properties, magnetic properties, thermal properties, optical properties, chemical properties, acoustical properties, radiological properties, and biological properties.

"Mechanical properties" refer to the response of a material to an applied load or force. Non-limiting examples of mechanical properties include Young's modulus, specific modulus, strength (e.g., tensile, compressive, shear, yield, bearing, creep), ductility, Poisson's ratio, hardness, impact toughness, resilience, fatigue/endurance limit, and fracture toughness.

"Electrical properties" refer to the response of a material to an applied electric or electromagnetic field. Non-limiting examples include electrical conductivity, electrical resistivity, permittivity, dielectric constant, dielectric (breakdown) strength, piezoelectric constant, and Seebeck coefficient.

"Magnetic properties" refer to the response of a material to an applied magnetic field. Non-limiting examples include permeability, hysteresis, and Curie point/temperature.

"Thermal properties" refer to a material's response to applied heat. Non-limiting examples include thermal conductivity, thermal diffusivity, coefficient of thermal expansion, emissivity, specific heat, melting point, glass transition temperature, boiling point, flash point, triple point, heat of vaporization, heat of fusion, pyrophoricity, autoignition temperature, and vapor pressure.

"Optical properties" refer to the response of a material to light. Non-limiting examples include absorptivity, reflectivity, refractive index, color, photosensitivity, transmissivity, and luminosity.

"Chemical properties" refer to the response of a material to a chemical environment. Non-limiting examples include pH, hygroscopy, surface energy, surface tension, reactivity, and corrosion resistance.

"Acoustical properties" refer to the response of a material to, or ability to generate, sound waves. Non-limiting examples include acoustic absorption and speed of sound.

"Radiological properties" refer to the response of a material to radiation. Non-limiting properties include neutron cross-section and specific activity.

"Biological properties" refer to the response of a material to an environment found in living animals and plants. Non limiting examples include toxicity.

"Phase" refers to a region of space throughout which the properties of a material occupying the space are approximately uniform.

"Composite" or "Composite material" refer to a material composed of two or more materials, where each material possesses a distinct phase at a length scale of interest (e.g., greater than atomic length scales) and a distinct interface is present between each of the two or more materials.

"Reinforced composite" refers to a composite including at least two phases, a matrix phase that is continuous and that surrounds at least a portion of a dispersed phase.

"Room temperature" refers to a temperature selected over the range of about 293 to 303 degrees Kelvin.

Embodiments of the present disclosure are directed to carbon-containing composites which are suitable for use as electrodes. Embodiments of the electrodes may be employed in any electrode application, including but not limited to, supercapacitors, secondary rechargeable batteries (e.g., lithium ion batteries), electrochemical sensors (e.g., glucose monitors, bio-analytic sensors), etc.

In an embodiment, the disclosed composites are reinforced composites that include a scaffold (i.e., the dispersed phase) and a porous carbon matrix (i.e., the matrix phase). The scaffold is formed from a plurality of graphene sheets and a plurality of carbon nanotubes, where the plurality of graphene sheets are generally planar (e.g., extending in an x-y plane). When the plurality of graphene sheets includes at least two graphene sheets, the at least two graphene sheets are approximately parallel to one another and separated out of plane (e.g., along a z-axis). The plurality of carbon nanotubes extend between the plurality of graphene sheets, where at least a portion of the plurality of carbon nanotubes are aligned in approximately at a defined angle with respect to the plurality of graphene sheets (e.g., approximately 0°, 45°, 90°, etc.). At least a portion of the scaffold is embedded within a porous carbon matrix (e.g., an activated carbon, a polymer derived graphitic carbon, etc.). The porosity within the matrix is generally continuous and extends throughout the entire composite. As a result, the composite is highly porous and, when utilized as electrode, exhibits an active surface area many times greater than that of existing electrodes, increasing performance of the composite electrode.

In one advantage, the scaffold acts to reinforce the porous matrix. As a result, the composite may be formed to greater thickness than can be achieved in electrodes formed purely from porous carbon that lack such reinforcement. With increased thickness, the surface area of composite electrodes may also be increased, resulting in enhanced charge storage of charge when employed in applications such as supercapacitors and batteries. Furthermore, the mechanical reinforcement afforded by the scaffold allows the composite to function as a free-standing electrode, without additional support.

In another advantage, the architecture of the composite porosity enhances the performance of electrodes formed from the composite. For example, the mean pore size of the substantially continuous matrix porosity decreases with distance inward from the surface of the composite. This pore geometry enhances mass transport through the pore network and increases the specific surface area of the composite as compared to porous networks having single-sized pores. The size of the pore network may be further varied to optimize electrode performance in different applications.

In further embodiments, the composite electrodes are easily fabricated as large area sheets. For example, the porous carbon, dispersion of graphene flakes, and a dispersion of carbon nanotubes are homogenously mixed in a solvent to form a viscous carbon slurry. The carbon slurry is deposited on a substrate to form a film of the carbon slurry, where the graphene flakes self-assemble to form the plurality of graphene sheets and the plurality of carbon nanotubes adopts a random orientation. Subsequently, a magnetic field is applied to the carbon slurry film, where the magnetic field lines are oriented at a defined angle with respect to the plurality of graphene sheets. The viscous slurry permits at least a portion of the carbon nanotubes to align approximately parallel with the magnetic field. Subsequent removal of at least a portion of the solvent solidifies the porous carbon matrix and fixes the relative positions of the plurality of graphene flakes and the plurality of carbon nanotubes.

As discussed in greater detail below, embodiments of the composite are suitable for use in a variety of electrical storage devices, such as supercapacitors and lithium ion batteries. The performance of supercapacitors and lithium ion batteries employing embodiments of the composite electrode was evaluated through cyclic voltammetry, and galvanostatic charge-discharge measurements. Measurements of performance of these devices confirm that embodiments of the fabricated composite electrodes having aligned carbon nanotubes possess higher electrode performance as compared to reference composites with unaligned carbon nanotubes and porous carbon alone. For example, composite electrodes demonstrated approximately 2.5 times to approximately 10 times improvement in specific capacitance and charge-discharge rates as compared to the unaligned composites and more than about 30 times improvement in specific capacitance and charge-discharge rates, as compared to an electrode of porous carbon alone.

Figure 1:
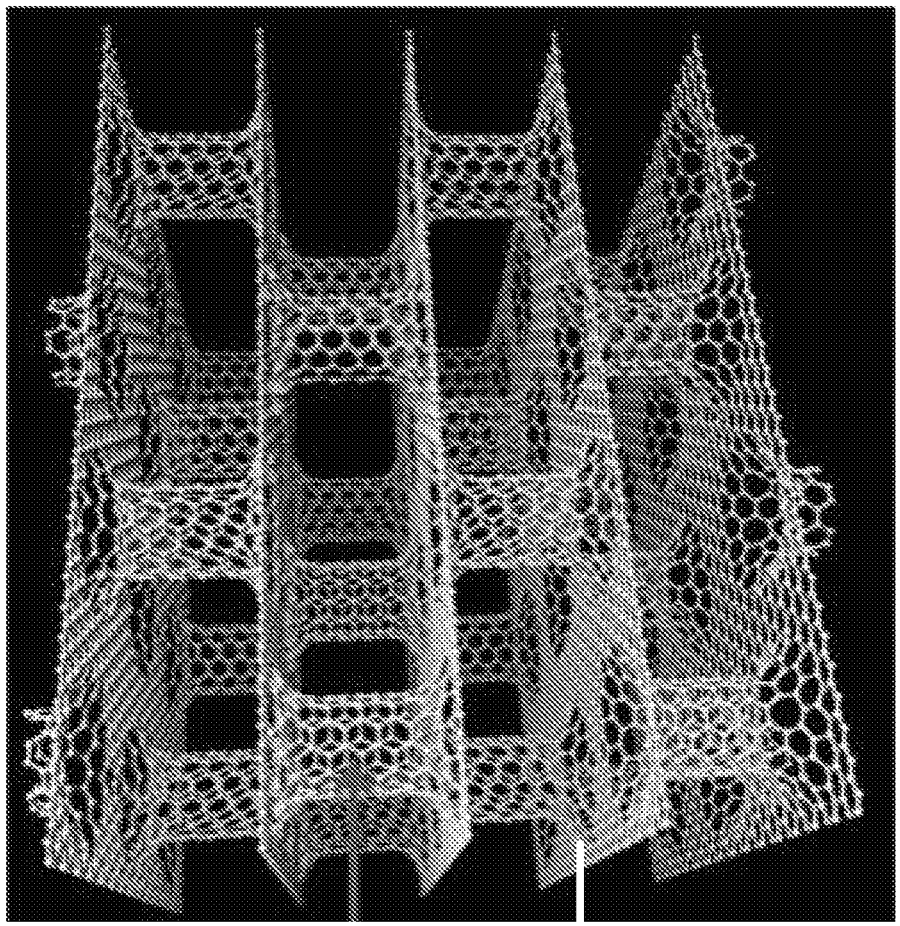
FIG. 1 is a schematic illustration of an idealized graphene-carbon nanotube structure.

While systems of graphene and carbon nanotubes have been proposed, embodiments of the disclosed composite differ significantly from these systems. A schematic illustration a proposed, 3-dimensional ideal graphene-carbon nanotube system (referred to below interchangeably as "3D-ideal") is shown in FIG. 1. The 3D-ideal system is formed by growth of graphene sheets, followed by inducement of holes in the sheets to grow carbon nanotubes there-through. The resulting structure covalently bonds the carbon nanotubes to the graphene sheets at the location of the induced holes, where the carbon nanotubes extend at 90° to the graphene planes.

Figure 2:
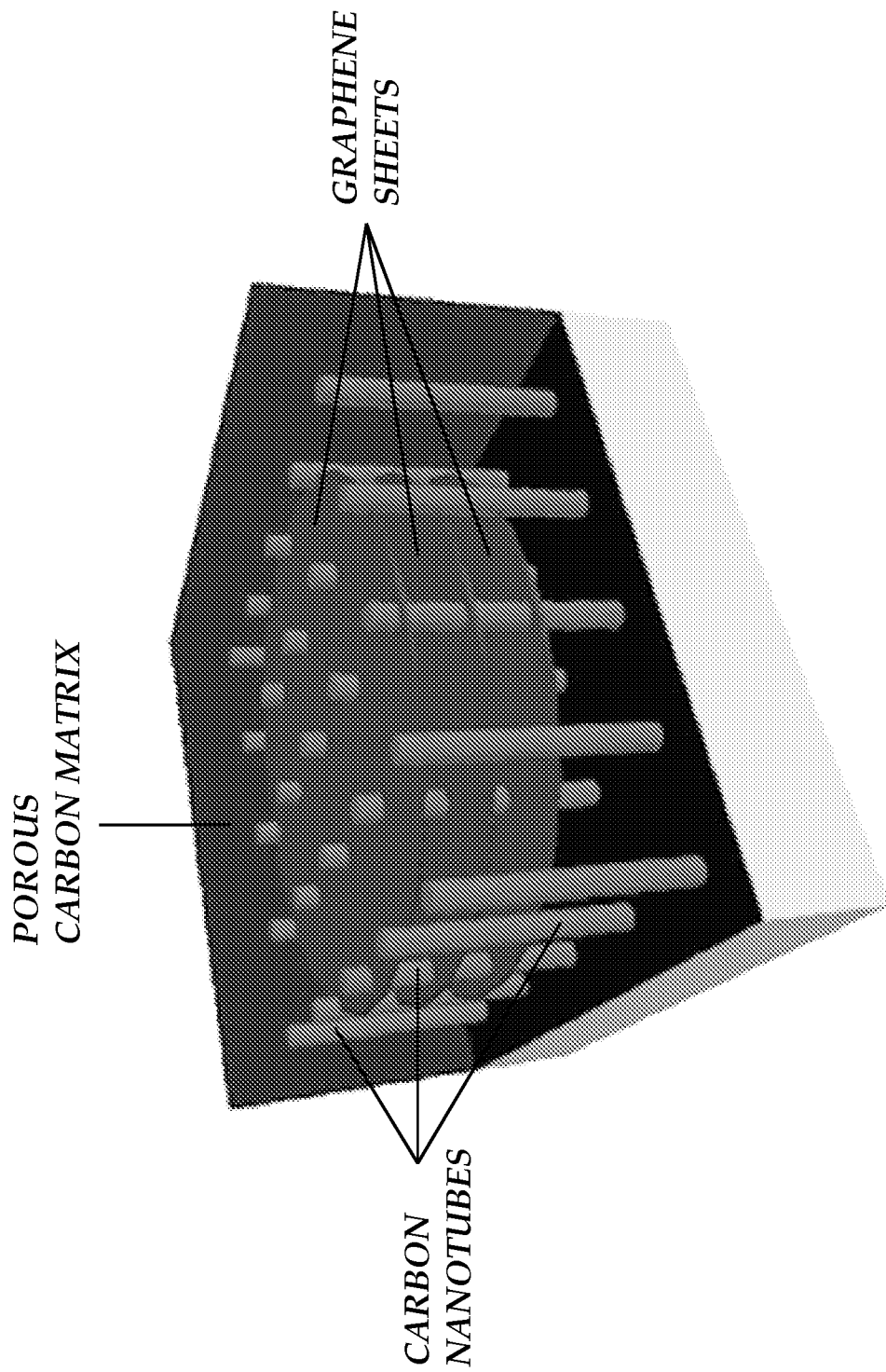
FIG. 2 is a schematic illustration of an embodiment of a composite film of the present disclosure.

In contrast, a schematic illustration of an embodiment of the composite of the present disclosure is shown in FIG. 2. As discussed in greater detail below, the composite of the instant disclosure is formed from a free mixture of graphene, carbon nanotube, and porous carbon. The graphene self-aligns in a plurality of sheets approximately parallel to a substrate upon which the mixture is deposited, while at least a portion of the carbon nanotubes are aligned at a defined angle to the graphene sheets. Thus, in one aspect, embodiments of the instant composite are different from the graphene-carbon nanotube system of FIG. 1 as they contain the porous carbon matrix in addition to the graphene-carbon nanotube structure. In another aspect, the angle between the graphene and carbon nanotubes is not fixed at 90° but may vary between about 0° to about 90°.

In a further aspect, the manner in which the carbon nanotubes are secured to the graphene sheets in embodiments of the disclosed composites is different from that of the graphene-carbon nanotube structure of FIG. 1. As discussed above, in the system of FIG. 1 the carbon nanotubes are covalently bonded to the graphene sheets. In contrast, embodiments of the disclosed composites include carbon nanotubes that are not covalently attached to the graphene. That is to say, the carbon nanotubes of embodiments of the instant disclosure are chemically distinct (i.e., a distinct phase) from the graphene sheets, as there is no chemical bond between the two. Without being bound by theory, the graphene sheets and carbon nanotubes may be connected to one another by a mechanical connection via the porous matrix. One example is as mechanical interlocking between at least a portion of the porous matrix and the scaffold. Another example is adhesion between the graphene sheets and the carbon nanotubes arising from van der Waals interactions. Such adhesion may be further facilitated by adhesion between each of the graphene sheets, the carbon nanotubes, and the porous carbon matrix. Embodiments of the composite may further include a binder to facilitate the adhesion.

Figure 3:
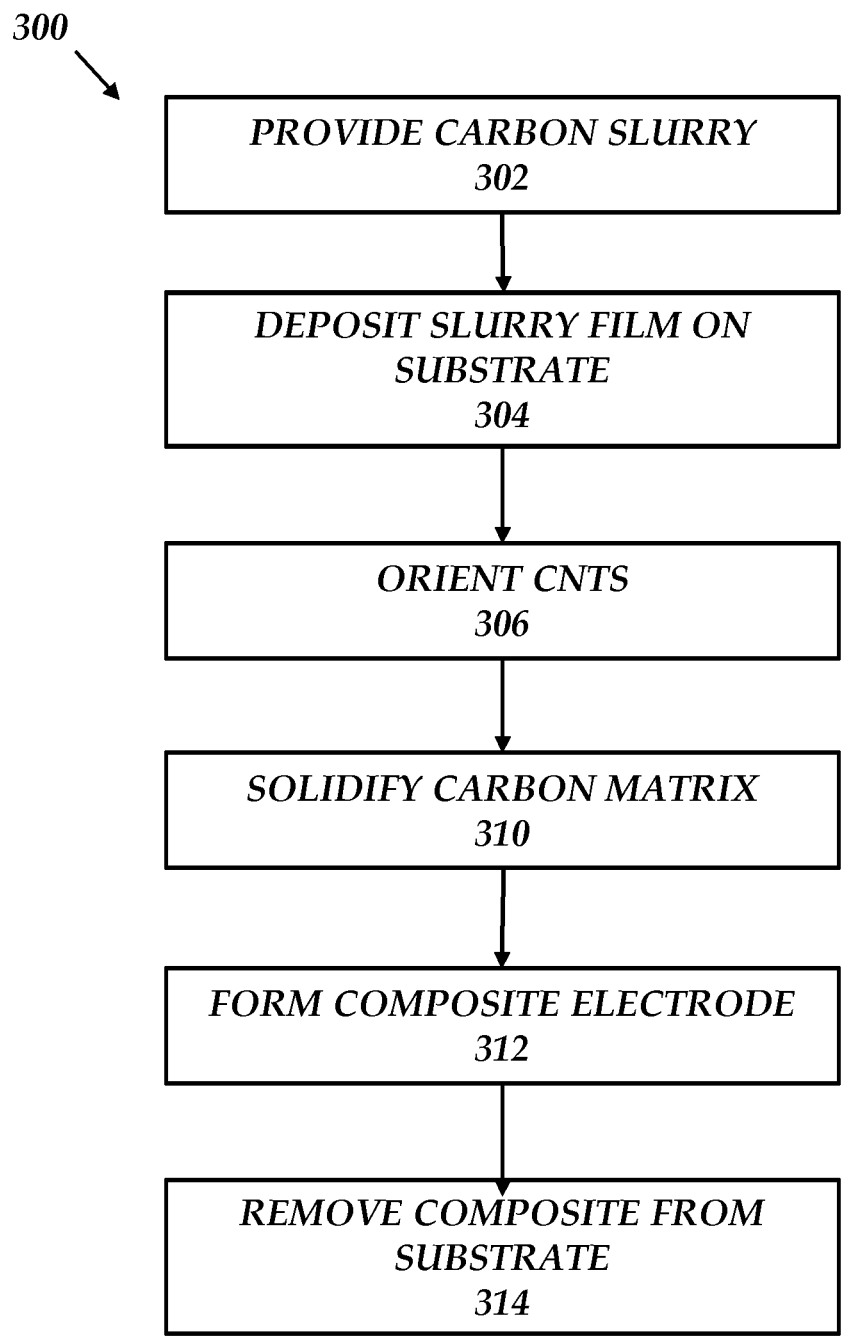
FIG. 3 is a flow diagram illustrating an embodiment of a method for fabricating composite films of the present disclosure
Figure 4E:
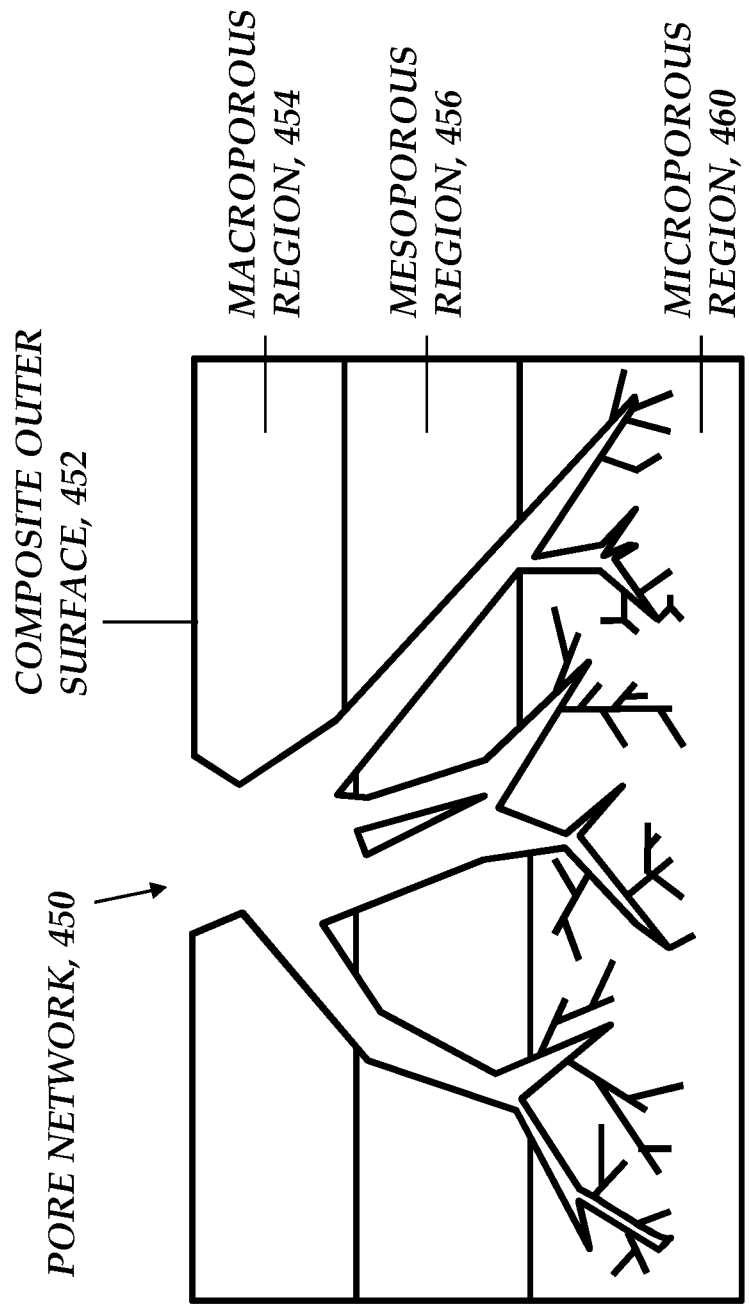
FIG. 4E is a schematic illustration of a continuous pore network of an embodiment of a composite film of the present disclosure.

Embodiments of the composite will now be discussed with reference to FIGS. 3 and 4A-4F. FIG. 3 is a block diagram illustrating an embodiment of a method 300 for fabrication of the graphene-carbon nanotube reinforced porous carbon composite. In operation 302, a carbon slurry is provided. In operation 304, a film of the slurry is deposited upon a substrate. In operation 306, the carbon nanotubes are oriented with respect to the graphene sheets. In operation 310, the composite film is solidified. Optionally, in operation 312, the composite film is removed from the substrate. It may be understood that alternative embodiments of the composite fabrication method may include greater or fewer operations and may be performed in any order without limit.

With reference to operation 302, a first embodiment of the carbon slurry includes porous carbon, a binder, a dispersion of the plurality of graphene flakes, a dispersion of a plurality of carbon nanotubes, and a first solvent. The porous carbon is added to a mixing vessel along with the binder, the graphene dispersion, and the first solvent to form a first carbon slurry precursor. The first carbon slurry precursor is mixed (e.g., with a stirrer) and subjected to a first sonication. The sonicated first carbon slurry precursor is added to the dispersion of carbon nanotubes is to form a second carbon slurry precursor. The second carbon slurry precursor is also mixed and subjected to a second sonication to form the carbon slurry.

In an embodiment of the composite, the porous carbon is selected from the group consisting of: pyrolysis products of carbonaceous materials and pyrolysis products of synthetic polymers. Examples of such carbonaceous materials include materials of vegetable origin including, but not limited to, wood, coal, peat, fruit stones, and shells. Examples of synthetic polymers include, but are not limited to, polyacrylonitrile (PAN), polystyrene, and phenolics.

Chars obtained from embodiments of these materials may be further activated. On activation these exhibit increased adsorption volumes of about 0.5 to about 1.1 $cm^3/g$ and surface areas within the range between about 700 $m^2/g$ to about 2500 $m^2/g$, depending on the manner of activation.

Activation may be performed chemically or physically. Chemical activation may be performed by impregnating activating agents within a slurry and carbonizing at temperatures within the range between about 600-1000° C. Examples of activating agents include, but are not limited to, phosphoric acid, zinc chloride, $H_2SO_4$, $K_2S$, KSNS, alkali metal hydroxide, and carbonate and chlorides of $Ca^{+2}$, $Mg^{+2}$ and $Fe^{+3}$). Physical activation may be performed by carbonizing a slurry of the porous carbon material at temperatures within the range between about 800 to about 1000° C. in presence of suitable oxidizing gases such as steam, $CO_2$, and air.

Embodiments of the porous carbon may also be functionalized. Examples of functionalizing groups may include, but are not limited to, carboxylic acid (—COOH), sulphonic acid (—SO$_3$H), amine (—NH$_2$), hydroxyl (—OH), and combinations thereof.

Embodiments of the binder are selected from the group consisting of polyvinylidene fluoride (PVDF), polyacrylonitrile (PAN), polytetrafluoroethylene (PTFE), carboxymethylcellulose (CMC), polystyrene, styrene-butadiene rubber (SBR), poly(ethylene oxide), functionalized graphene oxide, and silver paste.

In an embodiment of the composite, the dispersion of the plurality of graphene flakes includes the plurality of graphene flakes and a second solvent. The plurality of graphene flakes includes at least one of single layer graphene, multi-layer graphene, and reduced graphene oxide (RGO). A mean diameter of each of the plurality of graphene sheets is within the range between about 50 nm to about 75 µm. The second solvent may be N-butyl acetate, acetone, or diethylketone. The concentration of the graphene flake dispersion may be selected within the range between about 0.1 wt. % to about 5 wt. %. The number of graphene sheets may range from a monolayer graphene to about 10 layers.

In an embodiment of the composite, the dispersion of the plurality of carbon nanotubes comprises the plurality of carbon nanotubes and a third solvent. In certain embodiments, the third solvent is the first solvent. The plurality of carbon nanotubes comprises at least one of single-walled carbon nanotubes (SWNTs), double-walled carbon nanotubes (DWNTs), few-walled carbon nanotubes (FWNTs), and multi-walled carbon nanotubes (MWNTs). The plurality of carbon nanotubes may further comprise at least one of metallic and semiconducting carbon nanotubes. A mean diameter of each of the plurality of graphene sheets is within the range between about 0.8 nm to about 2 nm. A mean length of the plurality of carbon nanotubes is within the range between about 2 nm to about 20 nm.

In further embodiments, at least a portion of the plurality of carbon nanotubes is functionalized. The functionalization may include more functional groups selected from the group consisting of: carboxylic acid (—COOH), sulphonic acid (—SO$_3$H), amine (—NH$_2$), and hydroxyl (—OH) containing groups. The concentration of the carbon nanotube dispersion may be selected within the range between about 0.1 wt. % to about 5 wt. %.

Embodiments of the first and second sonication are performed by exposing the carbon slurry precursors to ultrasonic waves. Sonication may be performed at selected ultrasonic power density (at the transducer face), times, and duty cycle. For example, the frequency of the ultrasonic waves is selected within the range between about 20 kHz. The ultrasonic total power is selected within the range between about 500 W to about 750 W. The sonication time is selected within the range between about 20 min to about 360 min The duty cycle is selected within the range between about 10% to about 60%.

In embodiments of operation 304, a carbon slurry film 402 is deposited on a substrate 400 (FIGS. 4A-4B). Embodiments of the substrate 400 may comprise carbon coated copper, a flexible graphite film, carbon coated aluminum or nickel. Deposition methods may include, but are not limited to, doctor blade coating, dip coating and spin coating. The thickness of the deposited carbon slurry film 402 is within the range between about 20 µm to about 500 µm.

Following deposition of the carbon slurry film 402 on the substrate 400, the graphene flakes self-assemble into a plurality of graphene sheets 404. The plurality of graphene sheets 404 comprise of one or more abutting graphene flakes and are approximately planar. As illustrated in FIG. 4B, in certain embodiments, the plane of one or more of the plurality of graphene sheets 404 may extend approximately parallel to the surface of the substrate 400 (e.g., within an x-y plane). A distance separating respective ones of the plurality of graphene sheets 404 may be within the range between about 0.8 nm to about 2000 nm. Multi-layer graphene flakes, when present, may further self-assemble to form a larger noncontiguous film on the surface. Concurrently, the carbon nanotubes 406A are randomly oriented with respect to the plurality of graphene sheets 404.

Following operation 304 the porous carbon matrix is in a "wet" state 408A. In certain embodiments, the "wet" carbon matrix 406A possesses sufficiently low viscosity so as to permit movement of at least a portion of the randomly oriented the carbon nanotubes 406A to an oriented state, as discussed in greater detail below. For example, the viscosity of the wet carbon matrix 406A is within the range between about 300 cp to about 1200 cp.

In embodiments of operation 306, at least a portion of the randomly oriented carbon nanotubes 406A are oriented with respect to the plurality of graphene sheets 404. For example, as illustrated in FIG. 4C, a magnetic field 410 is applied through the thickness of the carbon slurry film 402 and substrate 404 while the carbon matrix is in its wet state 408A. The magnetic field 410 is of sufficient strength to physically move and reorient at least a portion of the plurality of carbon nanotubes such that their respective tube axes align approximately parallel to the lines of the magnetic field 410. For example, embodiments of the magnetic field strength are selectable within the range between about 0.3 T to about 3T. The magnetic field 410 may be oriented at a defined angle with respect to the plurality of graphene sheets 404 by rotating the magnetic field axis. For example, embodiments of the defined angle are selectable within the range between about 0° to about 90°. The carbon slurry film 402 and substrate 404 are maintained within the magnetic field 410 for a time sufficient to orient at least a portion of the plurality of carbon nanotubes with the magnetic field 410. For example, the carbon slurry film 402 and substrate 404 are maintained within the magnetic field 410 for a time within the range between about 2 min to about 20 min.

For example, as further illustrated in the embodiment of FIG. 4C, the substrate 400 and the plurality of graphene sheets 404 are oriented approximately parallel to the x-y plane. The magnetic field 404 is oriented at approximately 90° degrees with respect to the plane of the plurality of graphene sheets 404 (e.g., approximately parallel to the z-axis). As a result, at least a portion of the plurality of carbon nanotubes are induced to move from their randomly oriented state (randomly oriented carbon nanotubes 406A) to an oriented state (oriented carbon nanotubes 406B) substantially parallel to the applied magnetic field lines (about 90° to the plurality of graphene sheets 404).

In operation 310, at least a portion of the solvents are removed from the carbon slurry film 402 to form composite 414 (FIG. 4D), including solidified carbon matrix 408 and the plurality of graphene sheets 404 and oriented carbon nanotubes 406B (collectively scaffold 416). The solidified carbon matrix 408 of the composite 414 substantially inhibits further motion of the plurality of graphene sheets 404 with respect and oriented carbon nanotubes 406B. So configured, two or more of the plurality of graphene sheets 404 are separated from one another by a distance within the range between about 0.8 nm to about 2000 nm. For example, the distance may extend along the axis approximately perpendicular to the plane of the substrate)

In certain embodiments, at least a portion of the solvents are removed from the carbon slurry film 402 by exposure to heat. In one embodiment, the carbon slurry film 402 is heated within the magnetic field 410. In another embodiment, the carbon slurry film 402 is removed from the magnetic field 410 and subsequently heated. In further embodiments, the carbon slurry film 402 is initially heated within the magnetic field 410 and subsequently removed from the magnetic field 410 and further heated. For example, the carbon slurry film 402 may be heated within the magnetic field 410 until the porous carbon matrix is substantially solidified, while still retaining some amount of solvent. Subsequent heating may be performed outside of the magnetic field to substantially remove all of the solvent. The carbon slurry film 402 may be heated by exposure to a heat source (not shown) such as a hot plate in contact with the substrate 400 or placement of the substrate 400 and carbon slurry film 402 within an oven (e.g., a vacuum oven). In an embodiment the carbon slurry film 402 is heated at temperatures selected within the range between about 100° C. to about 250° C. for times selected within the range between about 2 hr to about 12 hr.

Following solidification of the composite 414 in operation 310, the composition of the composite 414 is:
about 0.1% to about 5% carbon nanotubes
about 0.1% to about 5% graphene
about 70% to about 98.8% porous carbon
about 1% to about 20% binder
on the basis of the total weight of the composite.

In certain embodiments, solidified carbon matrix 408 includes an interconnected pore network 450, as illustrated in FIG. 4F. For example, the pore network 450 extends from about an outer surface 452 of the composite 414 to the embedded scaffold 416 (not shown). In an embodiment, a mean diameter of the pores of the pore network 450 decreases in size with distance from the outer surface of the composite 414. For example, the pore network 450 includes a macroporous region 454 positioned adjacent the outer surface of the composite 452, where the mean diameter of the pores is greater than 50 nm within the macroporous region 454. The pore network 450 further includes a mesoporous region 456 positioned inward of, and interconnected with, the macroporous region 454, where the mean diameter of the pores is within the range between less than 50 nm and greater than 2 nm within the macroporous region 454. The pore network 450 additionally includes a microporous region 460 positioned inward of the mesoporous region 456, where the mean diameter of the pores is less than 2 nm within the microporous region 460. In further embodiments of the composite 414, the specific surface area of the composite is within the range between about 700 $m^2/g$ to about 2500 $m^2/g$.

Following solidification of the carbon matrix in operation 310, the composite 414 is formed into an electrode in operation 312. For example, an electrode cutter may be employed to cut out electrodes from the composite 414 while on the substrate 400. Subsequently, the formed composite electrode and substrate may be incorporated into energy storage devices (e.g., electrochemical devices). In this context, the substrate 400 may serve as a current collector for the formed electrode.

Optionally, the composite 414 may be removed from the substrate 400 to form a freestanding composite electrode in operation 314. In an embodiment, the composite 414 and substrate 400 are soaked in an acid which reacts with the substrate 400, allowing the composite electrode to easily peel from the substrate. For example, in the case of a copper substrate, the composite electrode and copper substrate may be soaked in sulfuric acid for approximately 24 hours. Following removal of the substrate from the composite electrode, the composite electrode is cleaned (e.g., in acetone) and dried.

In an alternative embodiment of the method 300, a second embodiment of the carbon slurry is provided in operation 302. As compared to the first embodiment of the carbon slurry, the second embodiment of the carbon slurry omits the binder and substitutes a dispersion of a polymer precursor resin in a third solvent for the porous carbon, while the dispersion of the plurality of graphene flakes, the dispersion of a plurality of carbon nanotubes, and the first solvent are unchanged. Carbonization of the polymer precursor resin yields the porous carbon matrix, as discussed in greater detail below. Embodiments of the polymer precursor resin are selected from the group consisting of polyacrylonitrile (PAN) and polystyrene. Embodiments of the third solvent are selected from PDVF or N-methyl pyrrolidone (NMP). In further embodiments the concentration of the polymer precursor resin within the dispersion is selected within the range between about 12 wt. % to about 30 wt. %.

The polymer precursor dispersion is added to a mixing vessel along with the graphene dispersion and the first solvent to form the first carbon slurry precursor. The first carbon slurry precursor is mixed (e.g., with a stirrer) and subjected to a first sonication. The dispersion of carbon nanotubes is subsequently added to the sonicated first carbon slurry precursor to form a second carbon slurry precursor. The second carbon slurry precursor is also mixed and subjected to a second sonication to form the second embodiment of the carbon slurry. Further processing of the second embodiment of the carbon slurry to deposit the slurry on the substrate 400 and align the carbon nanotubes is unchanged in operations 304 and 306.

In operation 310, the carbon slurry film is heated to a temperature sufficient to carbonize the porous carbon precursor, forming the solidified porous carbon matrix. In an embodiment, heating may be performed to a temperature within the range between about 1200° C. to about 1400° C. Subsequent processing of the solidified composite film to form electrodes in operation 312 and, optionally, operation 314, are unchanged.

Figure 5:
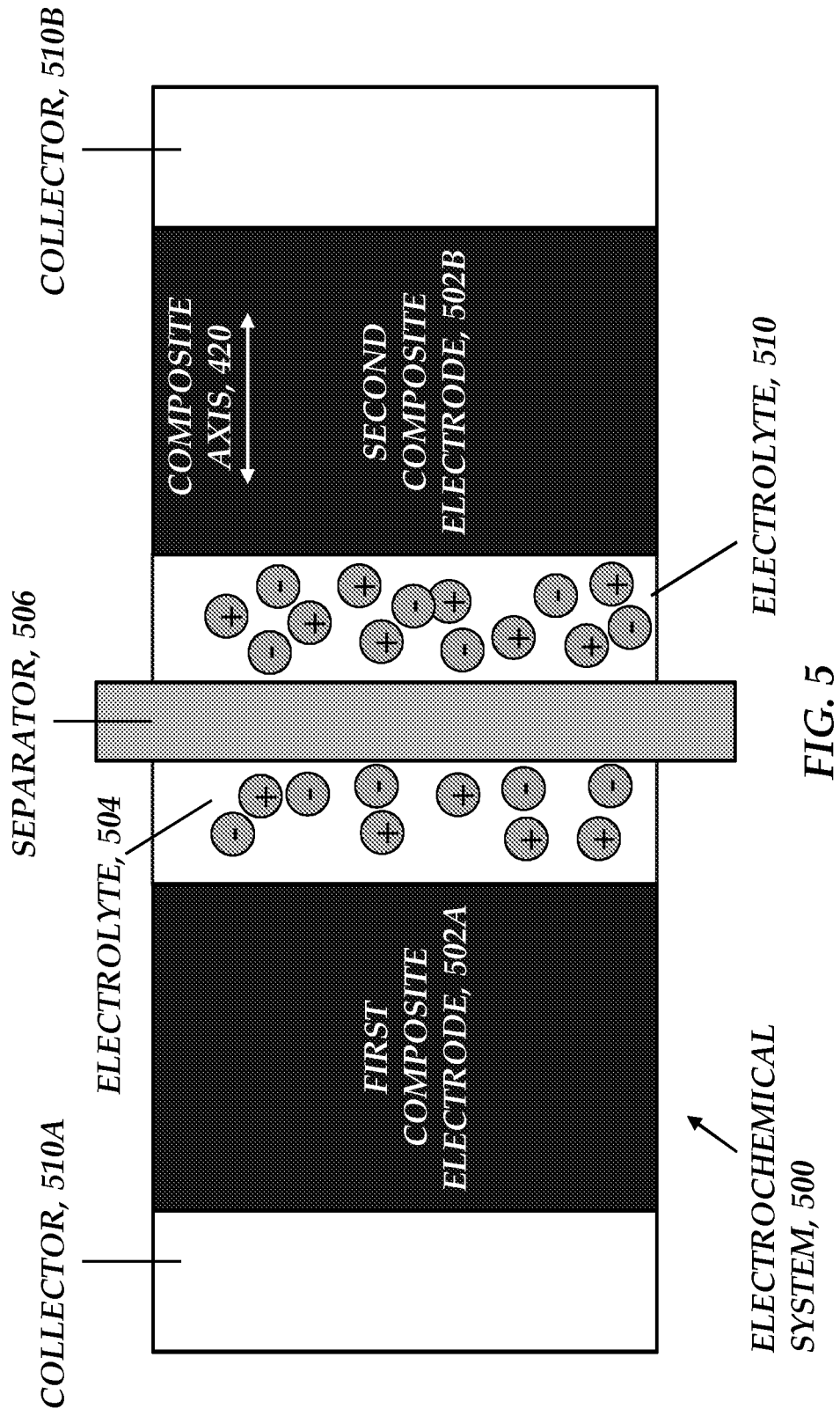
FIG. 5 is a schematic illustration of an embodiment of a supercapacitor including embodiments of composite electrodes of the present disclosure.

With reference to FIG. 5, an electrochemical system 500 incorporating embodiments of the composite electrode is illustrated. In an embodiment, the electrochemical system is a supercapacitor. However, it may be understood that embodiments of the composite electrode may be employed in other electrochemical devices without limit. Examples include, but are not limited to, batteries, bio-analytic sensors, glucose monitors.

The system 500 includes first and second composite electrodes 502A, 502B, an electrolyte 504, and a separator 506. Optionally, the system 500 further includes first and second collectors 510A, 510B. The composite electrodes 502A, 502B are formed from the composite 414 as discussed above in FIGS. 4A-4D, where the composite axis 420 extends through the thickness of each of the electrodes 502A, 502B.

The electrolyte 504 is positioned between the electrodes 502A, 502B. In certain embodiments, the electrolyte 504 is an ionic liquid, such as a room-temperature ionic liquid (RTIL). In another embodiment, the electrolyte 504 is a solid electrolyte. In additional embodiments, the electrolyte 504 is not an organic electrolyte. In further embodiments, the electrolyte 504 is selected from the group consisting of: potassium hydroxide (KOH), sulfuric acid ($H_2SO_4$), 1-butyl-4-methylpyridinium tetrafluoroborate (4MBPBF$_4$), 1-ethyl-3-methylimidazolium trifluoromethanesulfonate (EMIMOTf), 1-ethyl-3-methylimidazolium tetrafluoroborate (EMIMBF$_4$), sodium sulfate (Na$_2$SO$_4$), 1-butyl-2,3-dimethylimidazolium bis(trifluoromethylsuphonyl)imide (BMMI-TFSI), N-butyl-N-methylpyrrolidinium bis(trifluoromethanesulfonyl)imide (PYR$_{14}$-TFSI), and 1-ethyl-3-methylimidazolium bis(trifluoromethane-sulfonyl)azanide (EMIM-TFSA).

The separator 506 mechanically separates the electrodes 502A, 502B. In certain embodiments, the separator is an ion-permeable membrane. In additional embodiments, the ion permeable membrane comprises one of a semi-permeable filter paper, paper, a semi-permeable glass-fiber filter, and a semi-permeable polymer filter. In further embodiments, the ion-permeable membrane possesses a mean pore size within the range between about 0.05 µm and 50 µm.

Optionally, the electrochemical device 500 includes the collectors 510A, 510B in electrical communication with the first and second composite electrodes 502A, 502B, respectively. The collectors 510A, 510B further allow electrical communication between the composite electrodes 502A, 502B and a circuit external to the device (not shown). In certain embodiments, the collectors 510A, 510B may be the substrate 400 upon which the composite electrodes 502A, 502B are formed for mechanical support. For example, embodiments of the collectors include, but are not limited to, of carbon coated copper, a flexible graphite film, carbon coated aluminum and nickel. In alternative embodiments, the collectors 510A, 510B are omitted and the first and second composite electrodes 502A, 502B are free standing.

Embodiments of the disclosed composite electrodes may further include a lithium compound embedded therein. The lithium compound may be selected from the group consisting of: lithium titanate (LiTi$_5$O$_{12}$) and lithium metal-orthosilicates (LiMSiO$_4$) where M is iron (Fe), manganese (Mn), or nickel (Ni). In an embodiment of lithium containing electrodes, the composition of the composite electrode may be as follows:
about 0.1% to about 5% carbon nanotubes;
about 0.1% to about 5% graphene;
up to about 2% porous carbon;
about 88% to about 99.8% lithium compound;
on the basis of the total weight of the electrode. In further embodiments, the composite electrode may include a binder in a concentration of about 0.1 wt. % to about 2 wt. %.

EXAMPLES

In the following examples, composite electrodes are fabricated according to embodiments of the methods discussed above. Electrochemical devices employing one or more of the composite electrodes, such as supercapacitors and lithium ion batteries, are further fabricated. Selected properties and performance metrics of the composite electrodes and electrical storage devices are further discussed.

Composite Electrode Fabrication

A composite electrode was fabricated according to embodiments of method 300. The carbon slurry included DMF as the first solvent, an activated carbon (by MTI Corp) as the porous carbon, PDVF as the binder, a graphene dispersion of 23 wt. % graphene flake (Graphene supermarket) in a second solvent of N-butyl acetate, a carbon nanotube dispersion of 0.1 wt. % -5 wt. % single-walled carbon nanotubes (Sigma Aldrich, OCSiAl TUBALL) in DMF.

Carbon Slurry Preparation:
An embodiment of the carbon slurry is prepared as follows:
Preparation of activated carbon (AC): About 15-20 g AC is added to a bun mill grinder. The grind setting is set to FINE and a set time of two hundred and thirty seconds. The grinding process is repeated five times. Subsequently, the AC is further ground by hand with a glass mortar and pestle for approximately five minutes in batches of about 2 g to about 4 g. Each batch of manually ground AC is added to a 250 mL flask until a total of approximately 11.5 g AC is present in the flask.
Addition of binder: About 1.4 g of PVDF is added to the 250 mL flask.
Addition of solvent: About 50 mL of DMF is added to the 250 mL flask.
Mixing first carbon slurry precursor: The mixture of AC, PVDF, and DMF is mixed with a stirring rod to mix the slurry for approximately three minutes. The vial is closed and bath sonicated for 30 minutes (Branson Digital Sonifier, Model 450). The mixture of AC, PVDF, and DMF is further probe sonicated (about 2-4 W) for about 30 minutes with an approximately 5 s on/10 s off interval at about 30% power.
Addition of graphene: Using a micropipette, about 0.59 g of the homogenous graphene dispersion is added to the 250 mL flask.
Prepare first carbon slurry precursor: The mixture of AC, PVDF, DMF, and graphene dispersion is probe sonicated (about 700W) in a second sonication for about two hours with an approximately 5 s on/10 s off interval at about 30% power. The sonicated second carbon slurry precursor is further mixed with a stirring rod approximately 30 minutes and subjected to another sonication for about one hour using the same sonication parameters as in the second sonication above.
Preparation of carbon nanotubes: About 0.02 g SWNTs are added to a 20 mL vial. Using a micropipette, about 2 mL DMF is added to the vial. The SWNTs and DMF are probe sonicated (about 700 W)for about thirty minutes with an approximately 5 s on/10 s off interval at about 10% power. To prevent settling, bath sonication of the 250 mL vial containing the AC, PVDF, Graphene, and DMF is performed concurrently with the 30 mL vial.
Prepare second carbon slurry precursor: Add 9.5 g of the second carbon slurry precursor to the 20 mL vial with the SWNTs and DMF.
Complete carbon slurry: Probe sonicate (about 700 W) the second carbon slurry precursor for about 30 minutes with about 5 s on/10 s off intervals at about 10% power. The composition of the carbon slurry so prepared is about 88% activated carbon, about 10% PVDF, about 1% graphene, and about 1% SWNTs.

Composite Electrode Formation:
Electrodes are formed from the composite slurry as follows:
Prepare carbon slurry for deposition: If the time since last sonication of the carbon slurry exceeds one hour, probe sonicate the carbon slurry (about 700 W) for about one hour with about 5 s on/10 s off intervals at about 70% power. Stir with stirring rod for about two minutes.
Prepare substrate for deposition: Cut out a rectangular piece of glass having dimensions of about 3 cm by about 4 cm. Cut out piece of carbon coated copper foil (CCCF) having dimensions of about 3 cm by about 2.7 cm for use as the substrate. Using Keaton tape, tape all four sides of the CCCF to the glass. The CCCF should not be centered—three edges of the glass should be close to three edges of the CCCF and one edge of glass should have about 1 cm of space without CCCF. Repeat this process for desired number of electrodes.

Deposit carbon slurry by dip or spin coating: Dip coating will form a composite film having a thickness of about 40-60 mm. Spin coating will form a composite film having a thickness of about 20-40 mm.

- Dip coating: Fill a dip coating chamber with the carbon slurry. Clip the glass piece on the edge without the CCCF. Align the substrate with the dip coating chamber. Set the dip coating speed to about 30 and lower the substrate into the chamber. At its deepest point, reverse the direction to remove the substrate from chamber. Let the carbon slurry drip off of the substrate for about three seconds, then unclip the substrate and place it flat on an absorbent surface (e.g., a paper towel) with the CCCF side facing upwards. Wipe off excess carbon slurry from the bottom of the substrate (e.g., with a paper towel). Place the substrate and deposited composite (referred to herewith as the sample) directly onto a heating rod in a magnetic field apparatus.
- Spin coating: On a spin coating apparatus (Laurrell, WS-650SZ-6NPP/LITE) choose Static and press Edit Mode. Set the following phases:
  - Phase 1: time: about 10 sec, speed: about 600 rpm, acceleration: about 60 rpm/s.
  - Phase 2: time: about 2 min, speed: about 600 rpm, acceleration: about 0 rpm/s.

Press Run Mode and turn on the vacuum pump. Place the glass and CCCF substrate onto spin coating apparatus, centering the CCCF piece, and press Vacuum to turn on the vacuum suction. Use a pipette to deposit the carbon slurry onto the exposed surface of the CCCF substrate. Close the lid and press Start. Once spin coating has finished, open the lid, hold the edge of sample without CCCF, and turn off the vacuum suction by pressing Vacuum. Place the sample directly onto the heating rod in the magnetic field apparatus.
- Blade coating: On a blade coating apparatus (MTI Corp, MSK-AFA-III, Automatic thick film coater), a CCCF is placed and a coating is deposited in multiple iterations of the following operations until the desired thickness is achieved:
  - The carbon slurry is spread on the substrate using a blade at a speed of about 1 mm/sec to form a film of the carbon slurry.
  - The deposited carbon slurry film is subsequently dried using an overhead oven in preparation for deposition of another coating layer.

Align CNTs in magnetic field: Align the sample at about the defined angle with respect to the magnetic field atop the heating rod at about room temperature. Heat up the rod by turning the variable autotransformer up to about 30%. Leave the heat on for about 10 minutes, then let turn off the heat for about another 10 minutes, leaving the sample within the magnetic field alignment apparatus. Before removing sample, confirm that the carbon slurry has solidified completely. If not solidified, continue heating until solidification has occurred. Transfer the sample into a vacuum oven. To fabricate carbon electrodes without alignment, put the sample onto a hot plate at about 150° Celsius for about 10 minutes without the magnetic field.

Remove remaining solvent from the carbon slurry: Position all samples in a vacuum oven, turn the oven ON, set the vacuum valve to OPEN and the purge valve CLOSED. Turn on the vacuum pump. Set the temperature to about 250° C. and to auto-stop after about two hours. Once this heating operation has finished, allow the samples to cool to about room temperature and subsequently remove the samples from the vacuum oven.

Form composite electrode from deposited composite film: Remove the CCCF substrate and carbon electrode from the glass by peeling off the Kapton tape. Mount the sample within an electrode cutting apparatus (MTI Corp, MSK-T-09-LD) and secure in place. Activate the cutting apparatus to punch out a circular electrode. Use the same method to cut a separator for use in forming electrical storage devices, as discussed in greater detail below.

Scaffold Orientation

The ability to form composites including embedded scaffolds is verified. In particular, electron microscopy and Raman spectroscopy are employed to evaluate the orientation of the plurality of graphene layers oriented the plurality of carbon nanotubes. As discussed in detail below, these observations and measurements confirm the ability to form scaffolds in which the plurality of graphene sheets are oriented approximately perpendicular to a composite axis (e.g., approximately parallel to the substrate surface) and the orientation of at least a portion of the plurality of carbon nanotubes are adjustable by varying the direction of the magnetic field extending through the composite slurry (e.g., operation 310 of method 300).

Figure 6A:
FIGS. 6A-6C and 7A-7D are scanning electron micrographs of embodiments of composite films having different carbon nanotube orientation.
Figure 6B:
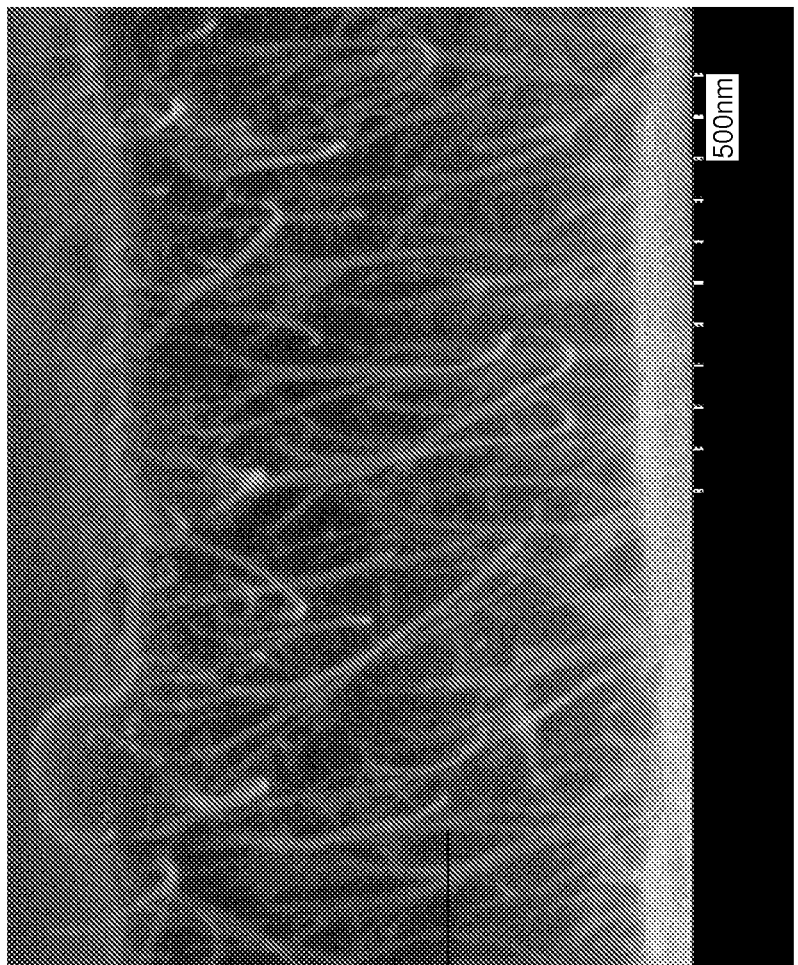
Figure 6C:
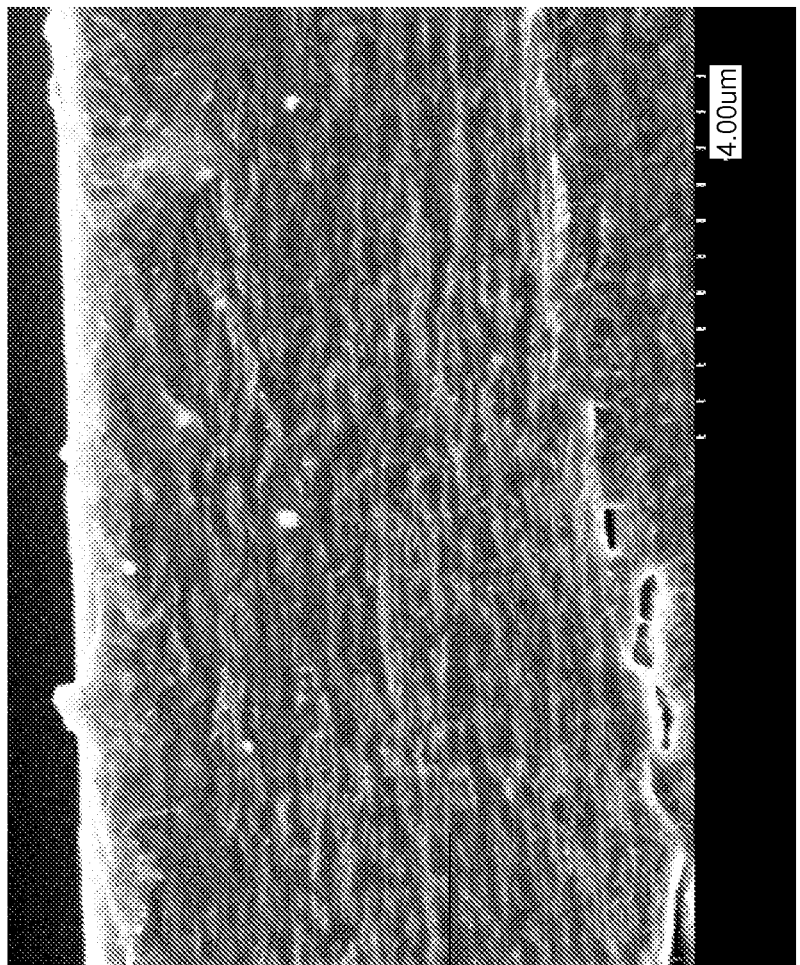

Scanning Electron Microscopy:

Scanning electron microscopy (SEM) images are acquired of composite electrodes formed according to embodiments of the disclosed methods (e.g., method 300). FIGS. 6A-6C illustrate the orientation of the carbon nanotubes and FIGS. 7A-7D illustrate the orientation of the plurality of graphene sheets.

Figure 7A:
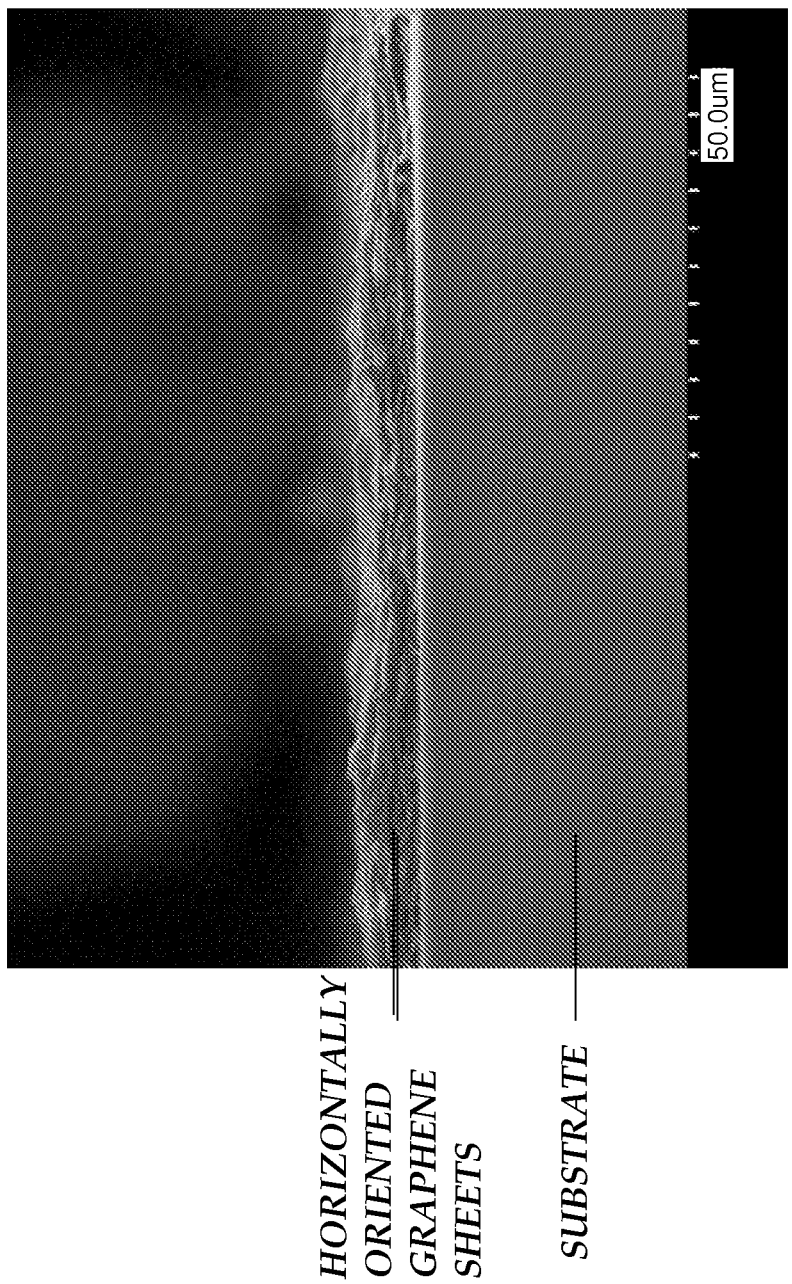
Figure 7B:
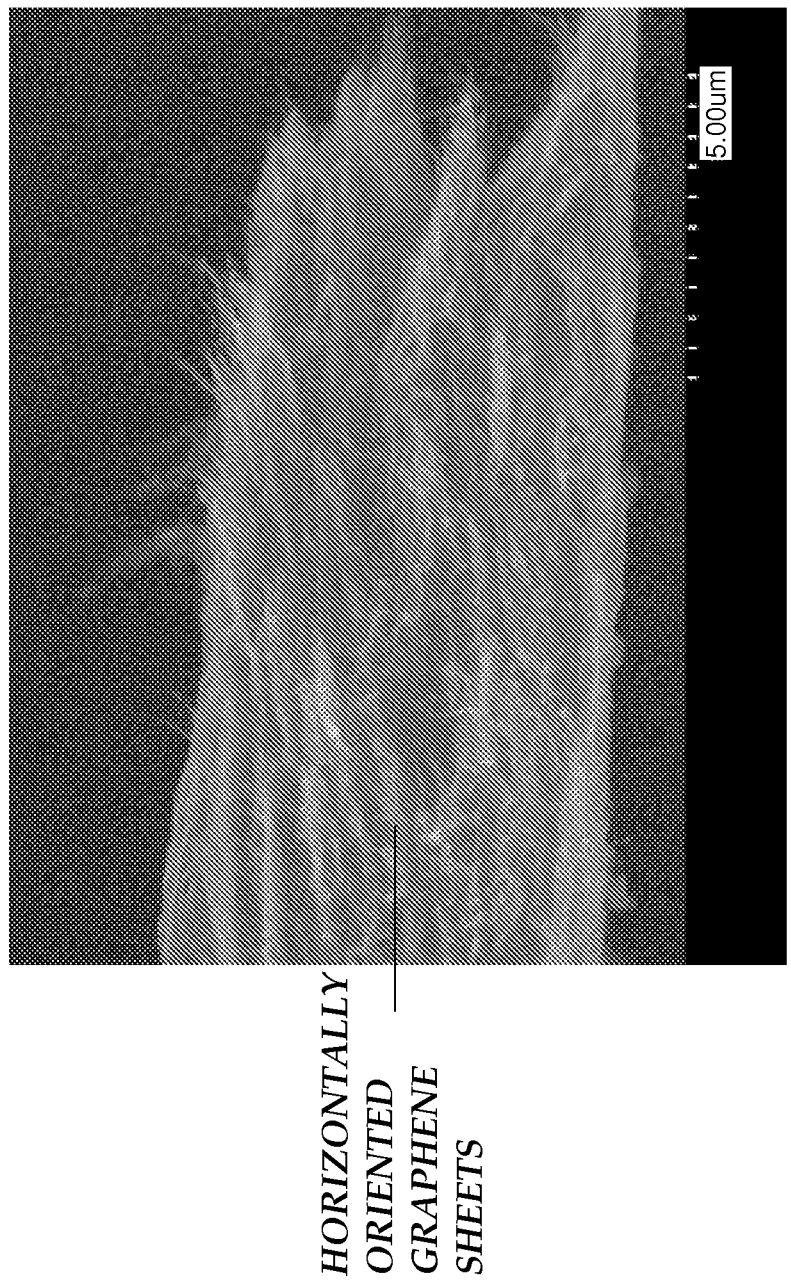

The composites of FIGS. 6A and 7A-7B are representative of embodiments of a composite electrode fabricated without employing a magnetic field to align the plurality of carbon nanotubes. It may be observed in FIG. 6A that the carbon nanotubes exhibit no preferred orientation and are approximately random. Concurrently, the plurality of graphene sheets is oriented approximately horizontally, that is approximately parallel to the substrate surface, as shown in FIGS. 7A-7B.

Figure 7C:
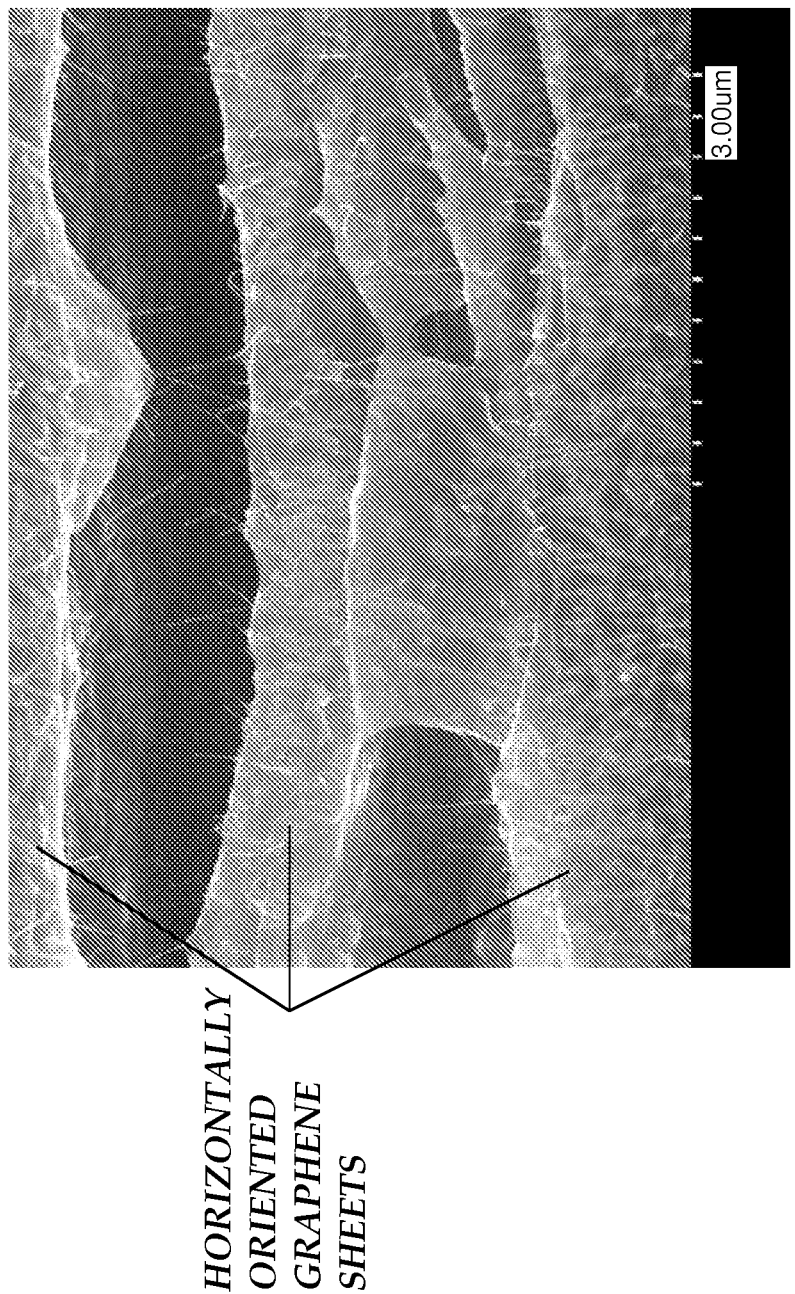
Figure 7D:
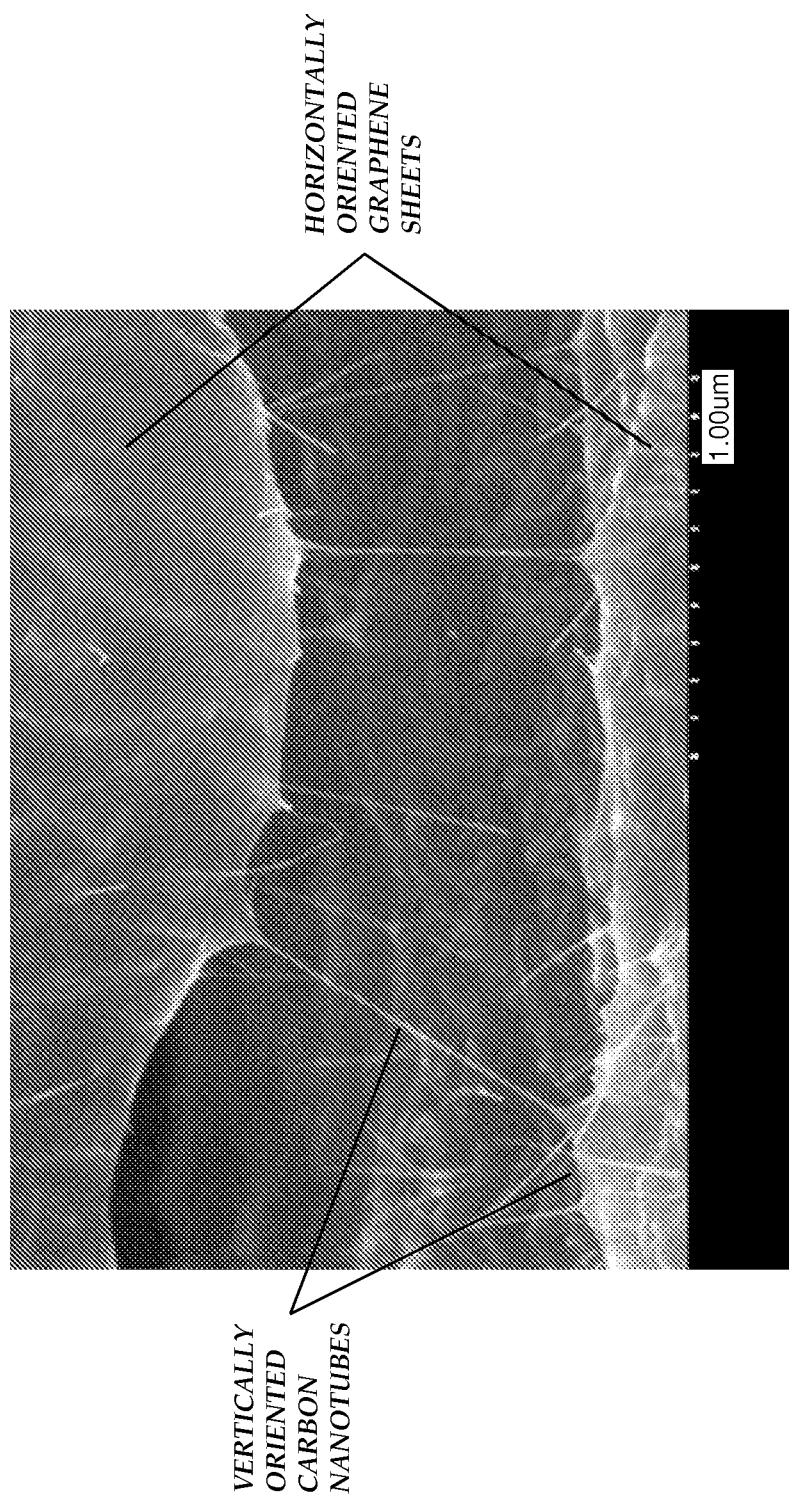

FIGS. 6B and 7C-7D illustrate a composite electrode fabricated with the magnetic field oriented approximately perpendicular to the substrate surface. It may be observed that the orientation of the carbon nanotubes is approximately vertical (FIG. 6B). Concurrently, the plurality of graphene sheets is oriented approximately horizontally, that is approximately parallel to the substrate surface (FIGS. 7C-7D).

FIG. 6C illustrates a composite electrode fabricated with the magnetic field oriented approximately parallel to the substrate surface. The observed orientation of the carbon nanotubes illustrated in FIG. 6C is approximately horizontal, approximately parallel to the substrate surface.

These images clearly demonstrate the efficacy and efficiency of magnetic field alignment of the plurality of graphene sheets and at least a portion of the plurality of carbon nanotubes within the porous carbon matrix.

Polarized Raman Spectroscopy:

These observations are confirmed through use of polarized Raman spectroscopy. In general, Raman spectroscopy is a characterization technique that illuminates a target sample with laser light (e.g., monochromatic light such as laser light) measures the frequency and intensity of the light reflected from the sample. The laser interacts with molecular vibrations, shifting the energy (frequency) of the laser light, which allows observation of vibrational and rotational characteristics of chemical bonds of the target. Raman spectrum are typically presented as a plot of intensity (y-axis) and wavenumber (x-axis), where the wavenumber is the difference between the inverse of the initial and reflected wavelength and is given in units of inverse length. In the context of carbon nanotubes, vibrations of the C—C bonds manifest in the Raman spectrum as a plurality of intensity peaks at about 1580 cm$^{-1}$ (the Raman "G-band").

In polarized Raman spectroscopy, a polarizer is inserted in the path of the laser light between the laser and the sample, allowing the polarization of the light to be selected by the operator. A first portion of the reflected light maintains the polarization of the incident light while a second portion of the reflected light adopts a polarization perpendicular to that of the incident light. Spectra are acquired for light polarized parallel to the incident light (0°) and perpendicular to the incident light (90°). Polarized Raman spectra using 532 nm as the excitation wavelength, exhibits a typical G band around 1535 cm$^{-1}$. The intensity of the Raman peak is at a maximum when the polarization direction of the excitation laser is aligned with the long axis of the carbon nanotubes, hence the electron polarizability axis. The intensity decreases as the polarization deviates from the long axis of the carbon nanotubes. The continually reducing intensity from horizontally aligned to 45 degree aligned to vertically aligned nanotubes clearly shows the influence of magnetic field in aligning the nanotubes.

Figure 8:
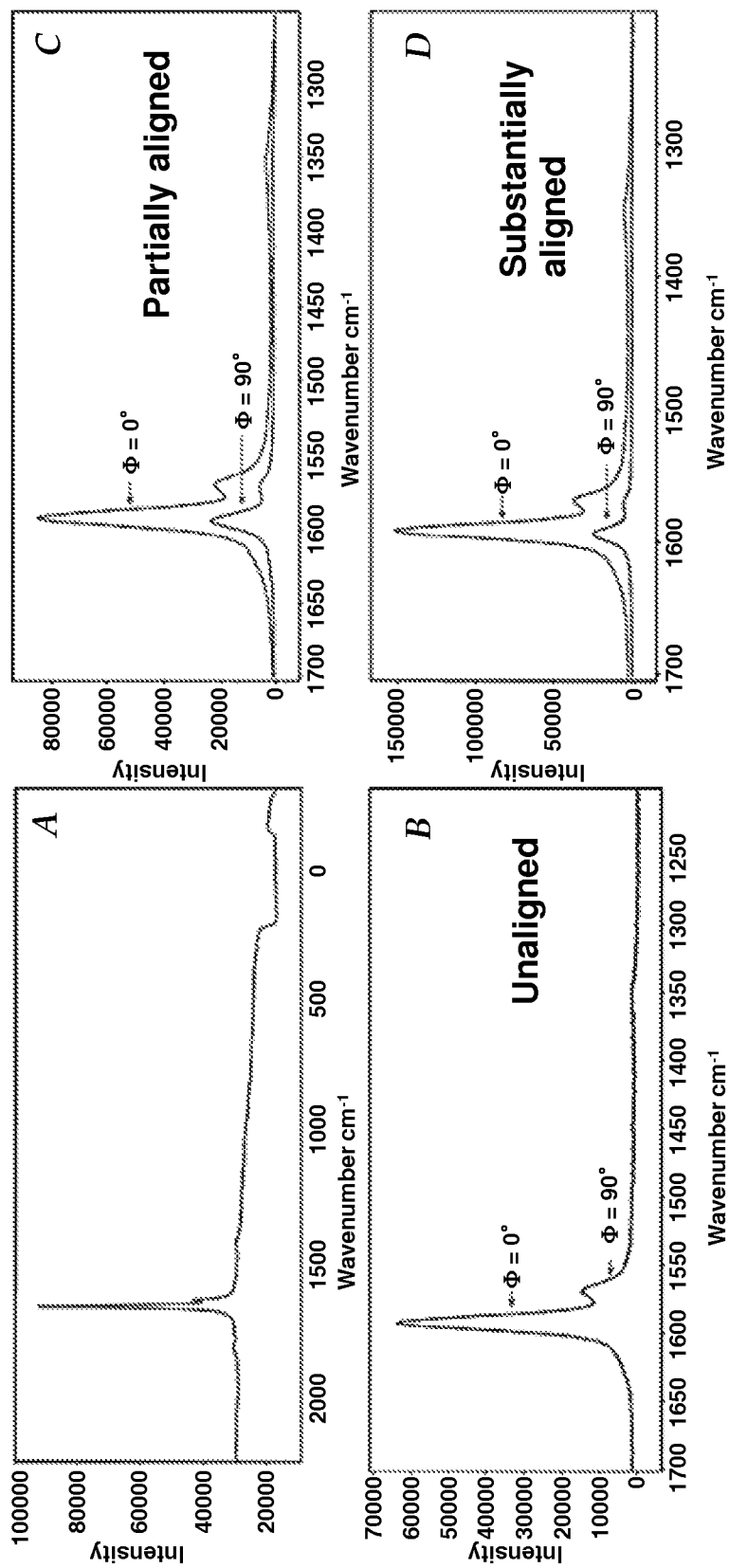
FIGS. 8A-8D are plots of intensity as a function of wavenumber for polarized Raman spectroscopy on embodiments of composite films having different carbon nanotube orientation.

Polarized Raman spectra are illustrated in FIGS. 8A-8D. FIG. 8A presents a Raman spectrum over a relatively large wavenumber range, showing the relatively sharp G-band peak. FIGS. 8B, 8C, and 8D present Raman spectra for embodiments of composite electrodes fabricated having different carbon nanotube alignments. The sample of FIG. 8B is fabricated without exposure to the magnetic field (Unaligned), while the sample of FIG. 8C is exposed to the magnetic field at an angle of about 45° to the composite axis (Partially aligned), and the sample of FIG. 8D is exposed to the magnetic field at an angle of about 90° to the composite axis (Substantially aligned). The unaligned composite electrode of FIG. 8B demonstrates almost equal intensity of Raman signal with incident polarization at 0° and 90° with respect to the plane of the composite film, confirming no net alignment or preferred orientation of nanotubes in the sample. The partially aligned composite electrode of FIG. 8C demonstrates an increase in the 0° intensity, as compared to FIG. 8B, confirming partial alignment of the carbon nanotubes. The substantially aligned composite electrode of FIG. 8D demonstrates an increase in the 0° intensity, as compared to FIG. 8C, further confirming successful alignment of the carbon nanotubes.

As with the SEM observations, the Raman measurements demonstrate the efficacy and efficiency of magnetic field alignment of at least a portion of the plurality of carbon nanotubes within the porous carbon matrix.

Supercapacitors

Supercapacitors incorporating embodiments of different electrode compositions and architectures are further fabricated from different substrates, separators, electrolytes, as well as varied orientation of the carbon nanotubes within the composite electrodes. The performance of the composite electrodes within these different supercapacitor systems is evaluated through measurement of cyclic voltammetry (CV) and galvanostatic charge-discharge (GCD). From these measurements, specific capacitance ($C_{sp}$), specific areal capacitance ($C_A$), coulombic efficiency (η), peak energy density ($E_v$), and power density (P) are further calculated. As discussed in greater detail below, it is observed that, composite electrodes having aligned carbon nanotubes exhibit improved capacitance over composite electrodes having randomly oriented carbon nanotubes.

Supercapacitor Formation:

Supercapacitor devices incorporating embodiments of the composite electrode are formed inside a swaging fitting (e.g., a Swagelock® cell) as follows. It may be understood that alternative embodiments of the supercapacitor devices may be formed as button cells or sandwich devices.

Prepare electrode-separator-electrode sandwich: The first (e.g., bottom) electrode is provided on the substrate/collector. The separator is placed upon exposed surface of the electrode. The separator is soaked with the electrolyte and the second (e.g., top) electrode is placed upon the electrolyte-soaked separator.

Assemble superconductor: The electrode-separator-electrode sandwich is centered inside a bottom Swagelok® cell compartment. An insulating ring (e.g., a plastic ring) is positioned upon the separator to inhibit short circuiting. A metal (e.g., stainless steel) plate is pressed on upon the second electrode and a top of the Swagelok® cell is screwed tightly to the bottom cell to ensure good contact between the electrodes and the collectors. When using ionic liquids as the electrolyte, the assembly process is carried out inside a Nitrogen glove box, and electrodes are heated at about 120° C. for at least thirty minutes to remove substantially all moisture.

Supercapacitor Performance:

Supercapacitors are formed as discussed above, with different substrates, separators, electrolytes, and electrode composition/architecture. Electrode configurations tested are:

Activated carbon and PDVF binder (AC)
Activated carbon, PDVF binder, and graphene (ACG)
Activated carbon, PDVF binder, graphene, and randomly oriented carbon nanotubes (ACGN)
Activated carbon, PDVF binder, graphene, and carbon nanotubes aligned at about 45° to the composite axis (ACGN45)
Activated carbon, PDVF binder, graphene, and carbon nanotubes aligned at about 90° to the composite axis (ACGN90)

Supercapacitor performance was evaluated by at least one of cyclic voltammetry (CV) and galvanostatic charge-discharge (GCD). In CV, the electrode potential is cyclically swept over a voltage range linearly in time and the current between the two electrodes is measured. The rate of voltage change over time during each of these phases is the scan rate (V/s). The data are plotted as current versus applied potential. In GCD, voltage as a function of time is measured for a constant current.

Specific capacitance of a supercapacitor is obtained according to Eq. 1.1:

$$C_{sp} = \frac{I}{m\frac{dV}{dt}} \quad (1.1)$$

Where I is the current in amps (A), m is the electrode mass in grams (g), and dV/dt is the rate at which voltage is changing. In the CV curve, the average current is determined by taking the integral over the curve and diving by two, while dV/dt is the scan rate. In GCD curves, the specific capacitance is determined by dividing the set current value by the slope of the discharge curve and the total electron mass.

Areal capacitance of a supercapacitor is obtained according to Eq. 1.2:

$$C_A = \frac{I}{A\frac{dV}{dt}} \quad (1.2)$$

where A is the area of one electrode.

Specific volumetric capacity of a supercapacitor is obtained by dividing $C_A$ by the electrode thickness, h, according to Equation 3:

$$C_v = \frac{C_A}{h} \quad (2)$$

Coulombic efficiency is obtained according to Equation 3:

$$\eta = \frac{t_{discharging}}{t_{charging}} 100 \quad (3)$$

Peak energy density is obtained according to Equation 4:

$$E_v = \tfrac{1}{2} C_v \Delta V^2 \quad (4)$$

where ΔV is the voltage difference of discharge.

Power density is obtained according to Equation 5:

$$P = \frac{E_v}{\Delta t} \quad (5)$$

where Δt is the discharge time.

(a) Substrate/Collector Optimization

Cyclic voltammetry tests were performed on supercapacitors with electrodes deposited upon substrates/collectors of carbon coated copper foil and graphite foil (Grafoil®). Free-standing composite electrodes, without a supporting substrate, were also tested. Testing was further conducted with two different electrolytes, 1M $H_2SO_4$ and 1-Ethyl-3-methylimidazolium tetrafluoroborate (EMIMBF$_4$). In each CV test, the voltage range was about 1V.

Figure 9A:
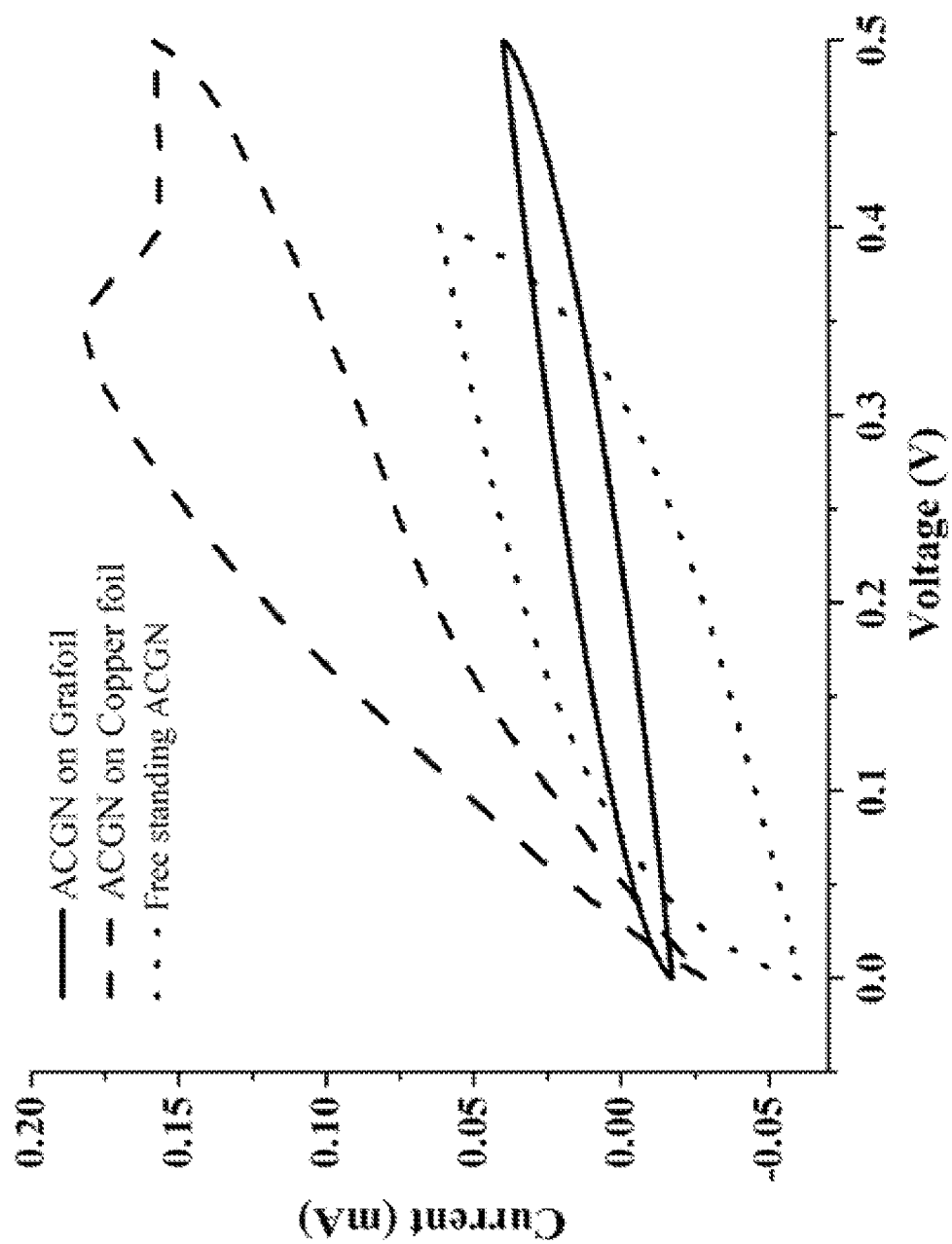
FIGS. 9A-9B are plots of CV measurements on embodiments of supercapacitors composed of ACGN and AC electrodes, respectively, on different substrates with H$_2$SO$_4$ and EMIMBF$_4$ electrolytes.
Figure 9B:
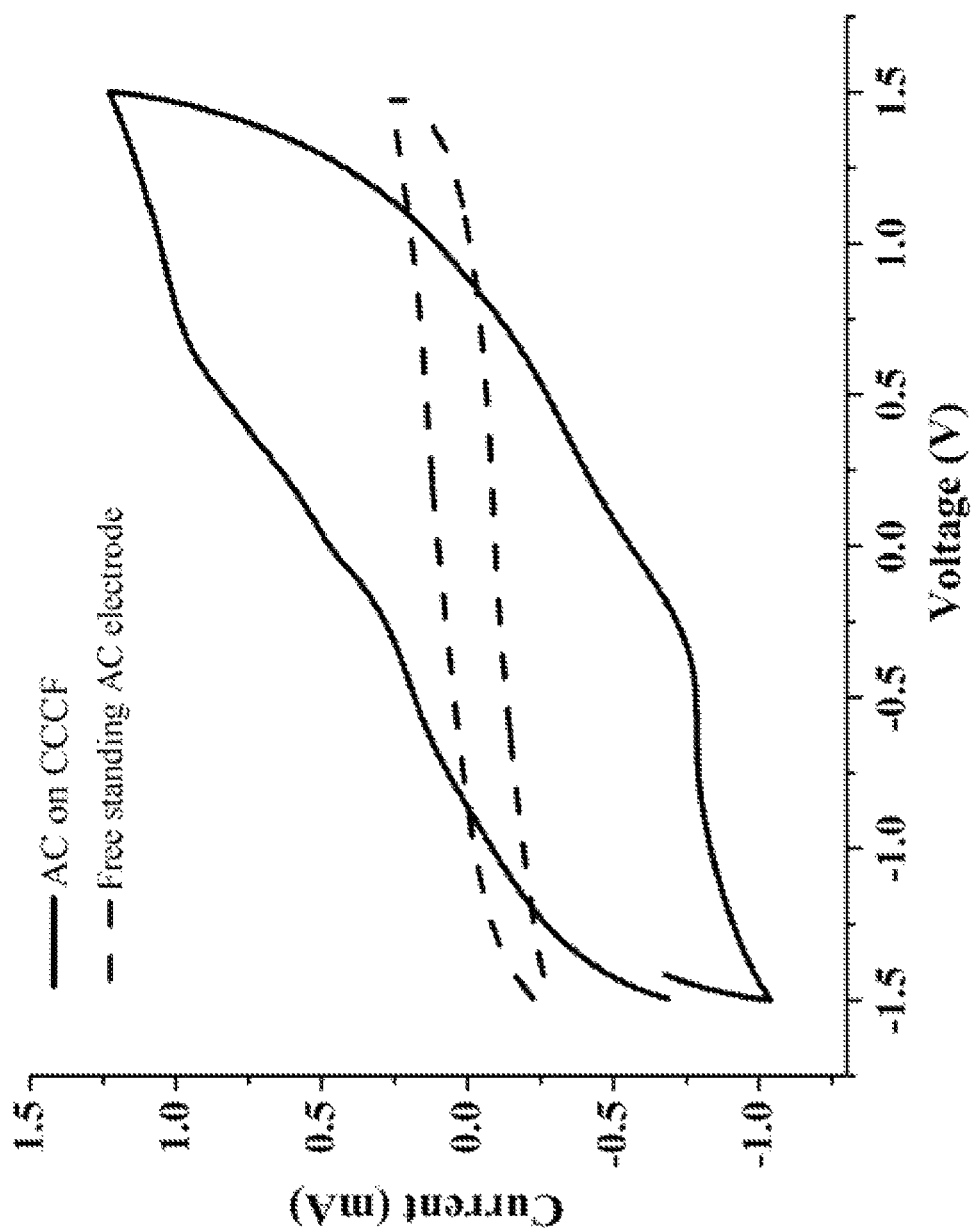

The results of the substrate/collector optimization testing are illustrated in FIGS. 9A and 9B. FIG. 9A illustrates the measured CV response of embodiments of supercapacitors composed of ACGN electrodes 1M $H_2SO_4$ as the electrolyte and the three different substrates. FIG. 9B illustrates the measured CV response of embodiments of supercapacitors composed of AC electrodes using EMIMBF$_4$ as the electrolyte and the three different substrates. These results illustrate that copper yields the highest capacitance values. However, the copper substrate/collector reacts with sulfuric acid when over 0.4 V is applied. Therefore, it may be concluded that freestanding films are the best option for comparisons between all electrodes but copper substrates/collectors are the best option for measuring the maximum capacitance values.

(b) Separator Optimization:

Cyclic voltammetry tests were performed on supercapacitors with electrodes separated by a Whatman® (size 1) filter paper, a Whatman® glass filter paper, a Celgard® separator, and a Millipore® (type GSWP) separator. Testing was further conducted with two different electrolytes, 1M $H_2SO_4$ and 1-Ethyl-3-methylimidazolium tetrafluoroborate (EMIMBF$_4$).

Figure 10A:
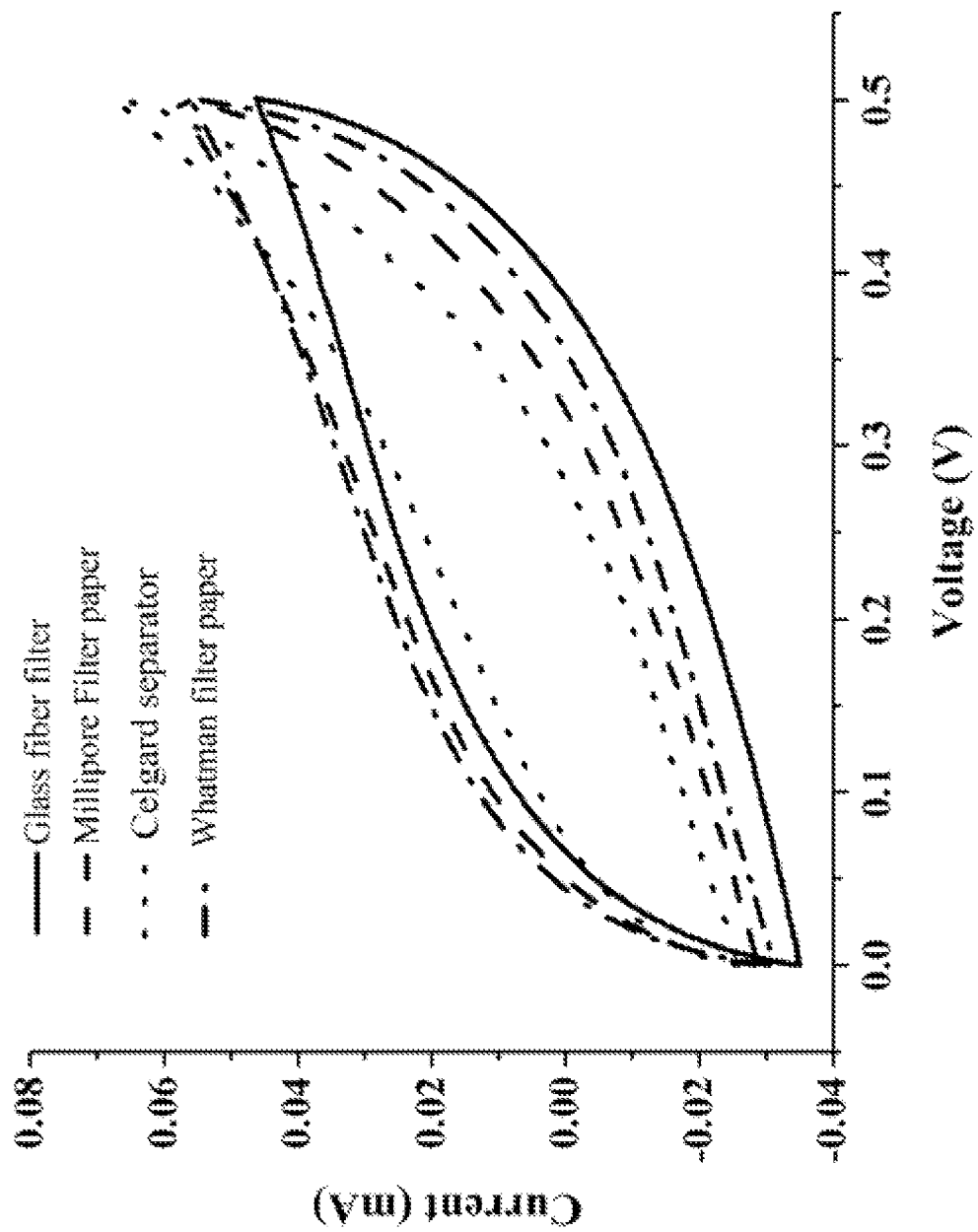
FIGS. 10A-10B are plots of CV measurements on embodiments of supercapacitors composed of free-standing ACGN electrodes and ACON90 electrodes on a carbon-coated copper substrate, respectively, investigating supercapacitor performance using different separators.
Figure 10B:
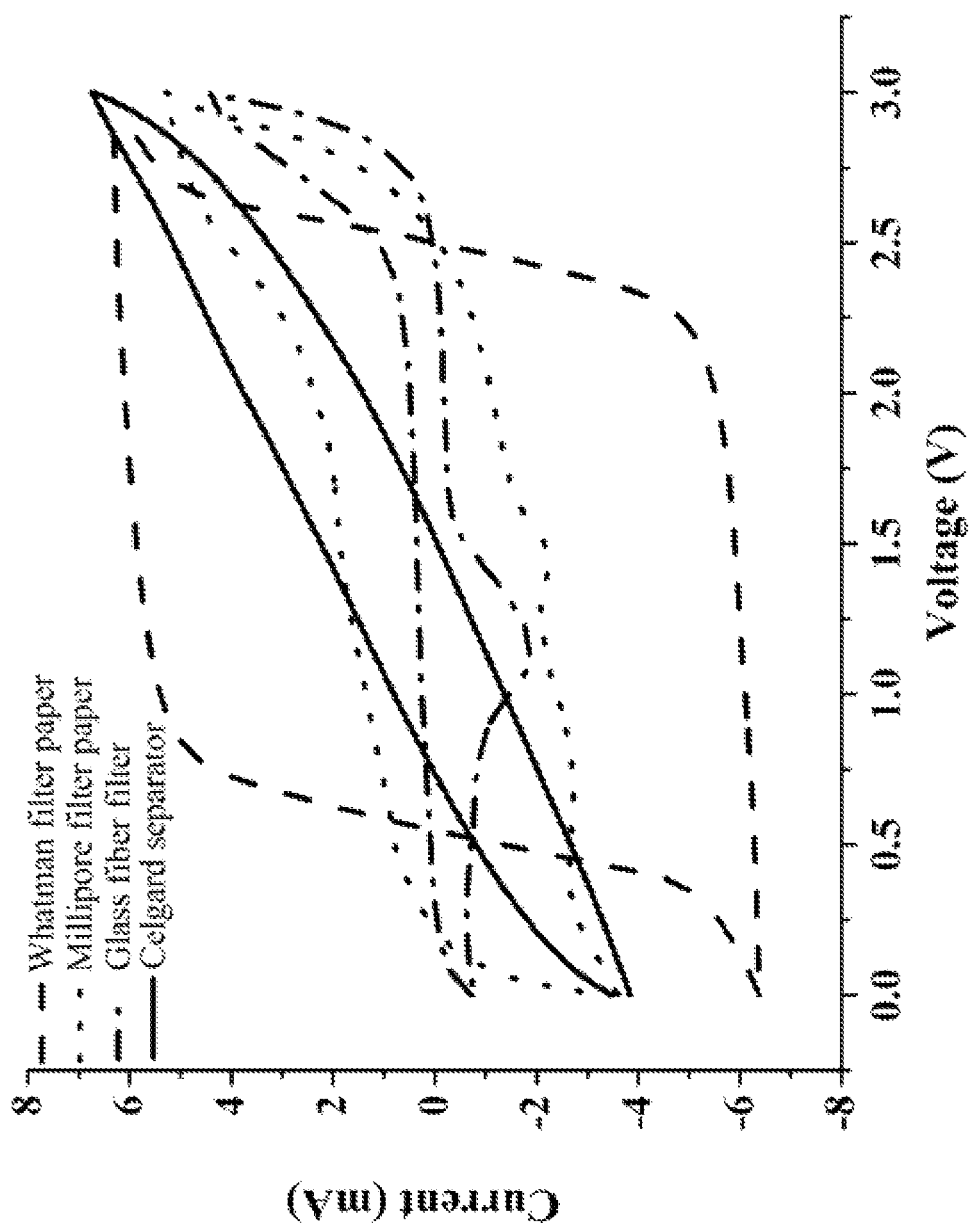

The results of the separator optimization testing are illustrated in FIGS. 10A and 10B. FIG. 10A illustrates the measured CV response for three separators using a free-standing electrode of activated carbon, PDVF binder, graphene, and randomly oriented carbon nanotubes (ACGN) and 1M $H_2SO_4$ as the electrolyte. FIG. 10B illustrates the measured CV response for the three substrate conditions using an electrode of activated carbon, PDVF binder, and graphene (ACG) on a carbon-coated copper substrate with EMIMBF$_4$ as the electrolyte. These results illustrate that the Whatman® filter paper provides the best partition between the electrodes. This is evident by the Whatman® filter paper having the most square-like and symmetric CV curves for both $H_2SO_4$ and EMIMBF$_4$. Although Whatman® filter paper was used as the main separator; other separators could be employed to manufacture Swagelock® cells for similar performance trends with embodiments of the three-dimensional composite electrodes.

(c) Scan Rate Optimization:

Changing the test scan rate portrays proper cyclic voltammetry behavior of supercapacitors. Increasing scan rates results in larger area within the curves and shows higher capacitance. Scan rates examined are 0.002 V/s, 0.005 V/s. 0.01 V/s, 0.015 V/s, 0.02 V/s, 0.03 V/s, and 0.05 V/s.

Figure 11A:
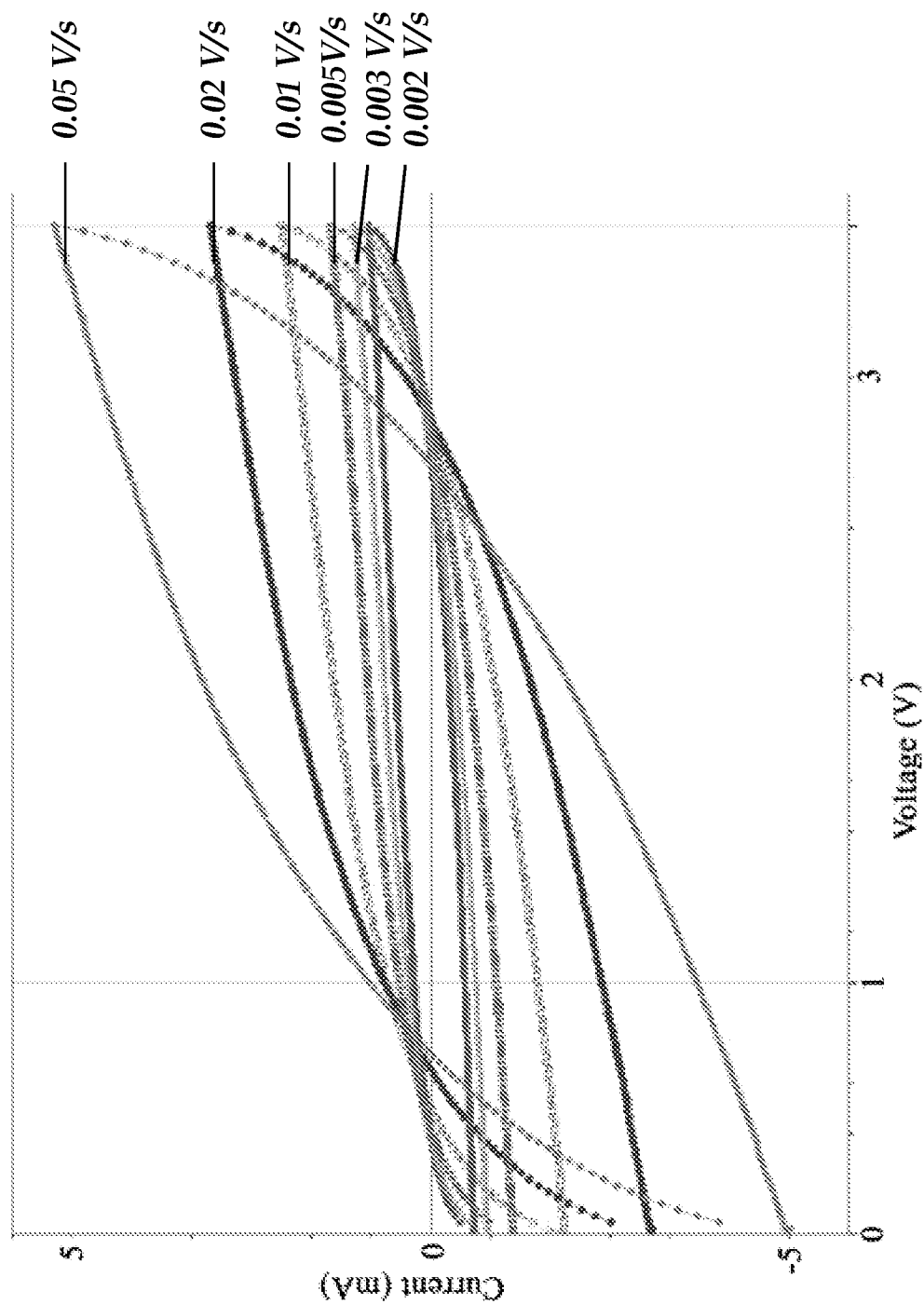
FIGS. 11A-11B are plots of CV measurements on embodiments of supercapacitors including an ACGN electrode and an ACGN90 electrode on carbon-coated copper, respectively, and a paper separator, investigating supercapacitor performance at different scan rates.
Figure 11B:
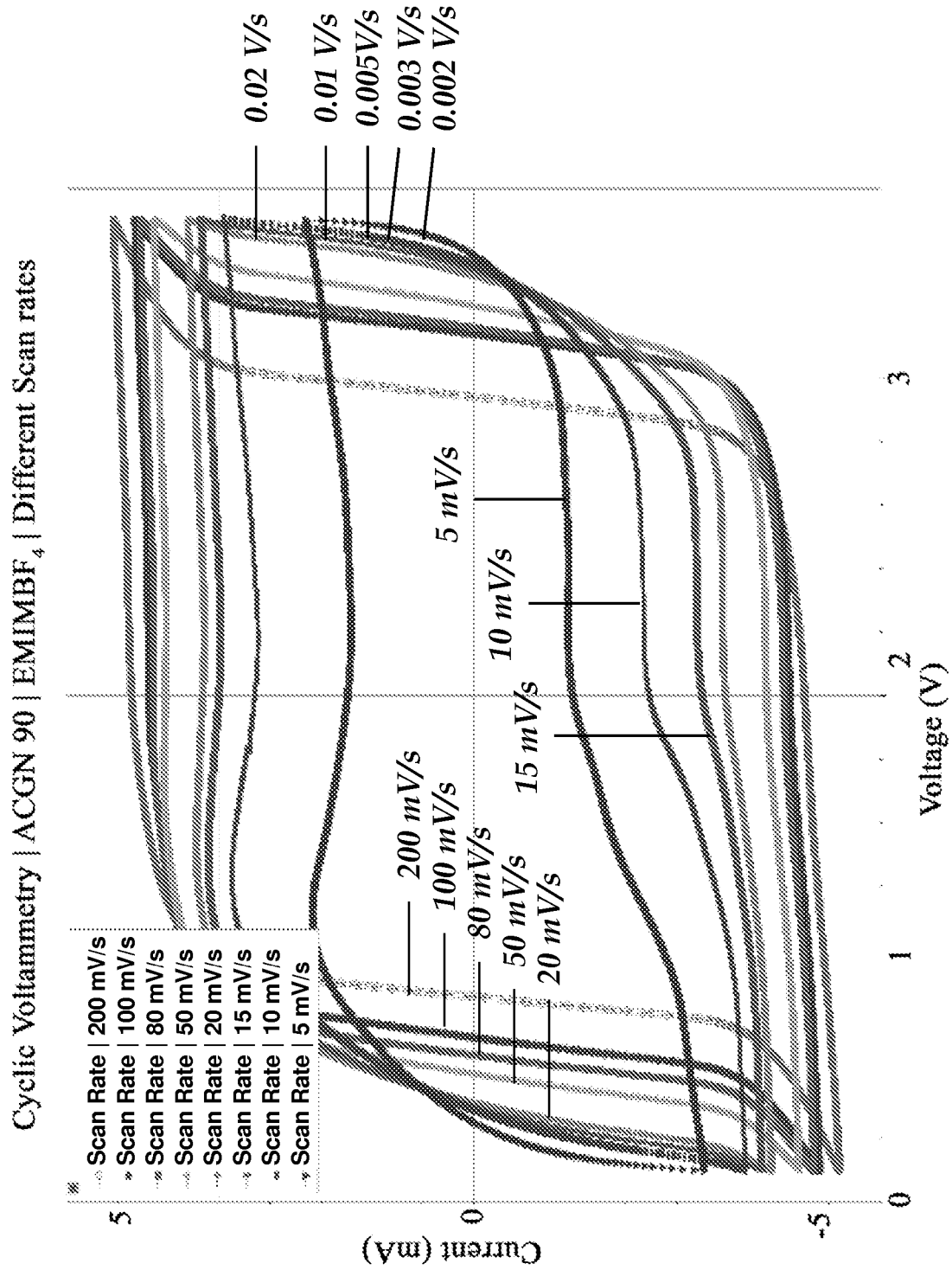

The results of the scan rate optimization testing are illustrated in FIGS. 11A and 11B. FIG. 11A illustrates the measured CV response for different scan rates using electrodes composed of activated carbon, PDVF binder, graphene, and randomly oriented carbon nanotubes (ACGN) on a CCCF substrate, with a filter paper separator, and 1M $H_2SO_4$ as the electrolyte. FIG. 10B illustrates the measured CV response for different scan rates using an electrode of activated carbon, PDVF binder, graphene, and carbon nanotubes aligned at approximately 90° to the composite axis (ACGN90) on a CCCF substrate, with a filter paper separator, with EMIMBF$_4$ as the electrolyte. The electrode system with vertically aligned carbon nanotube ACGN90 (FIG. 11B) shows much higher capacitance, which can be observed from the fact that it exhibits the greatest area under the CV curve.

Figure 12:
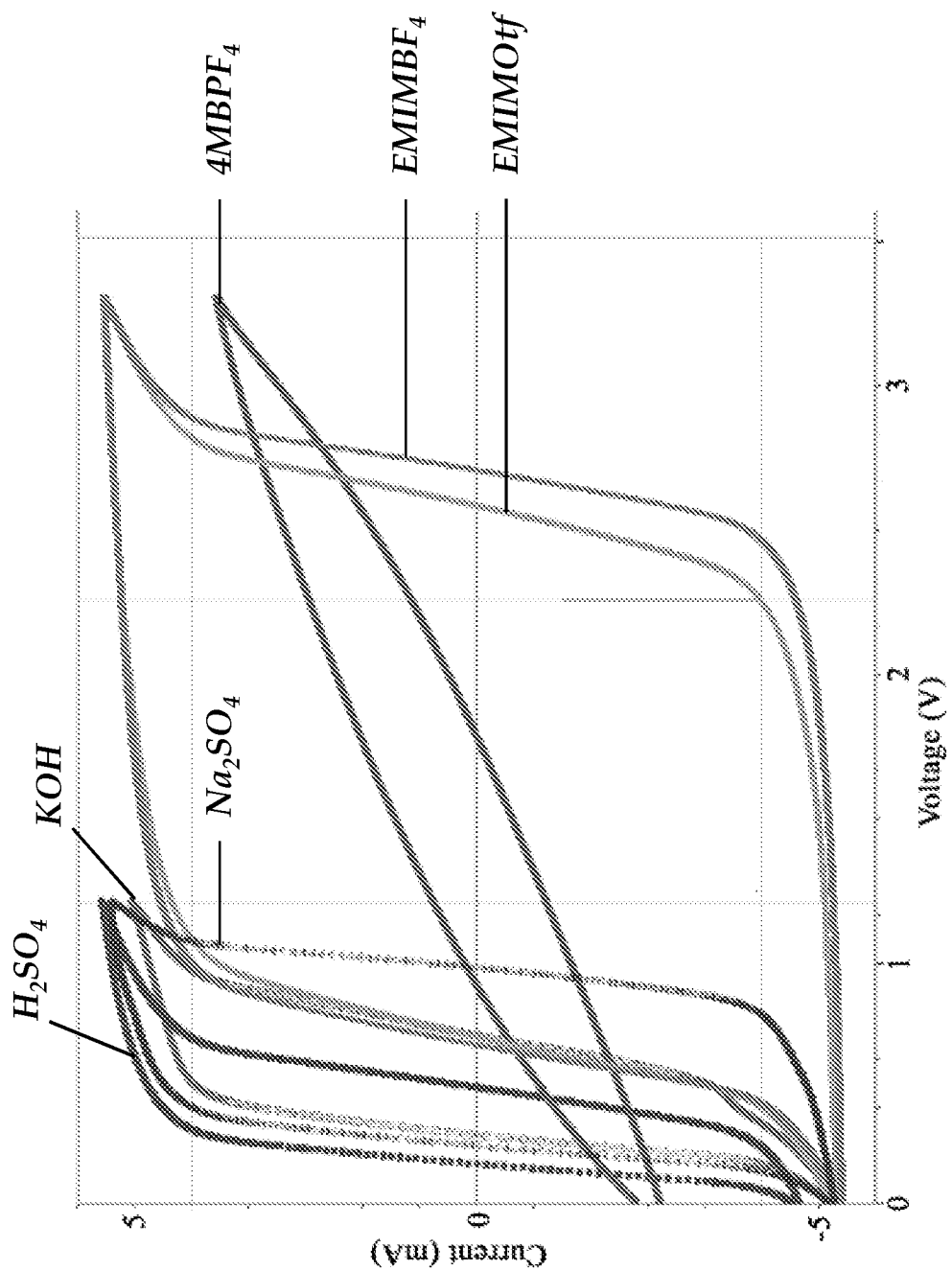
FIG. 12 is a plot of CV measurements on embodiments of a supercapacitor composed of ACG electrodes on a carbon coated copper foil substrate and a paper separator, investigating supercapacitor performance with different electrolytes.

(d) Electrolyte Optimization:

Cyclic voltammetry tests were performed on supercapacitors having ACG electrodes on a CCCF substrate, with a filter paper separator and illustrated in FIG. 12. Electrolytes examined are: potassium hydroxide (KOH), sulfuric acid ($H_2SO_4$), 1-butyl-4-methylpyridinium tetrafluoroborate (4MBPBF$_4$), 1-ethyl-3-methylimidazolium trifluoromethanesulfonate (EMIMOtf), 1-ethyl-3-methylimidazolium tetrafluoroborate (EMIMBF$_4$), sodium sulfate (Na$_2$SO$_4$), 1-butyl-2,3-dimethylimidazolium bis(trifluoromethylsuphonyl)imide (BMMI-TFSI), and N-butyl-N-methylpyrrolidinium bis(trifluoromethanesulfonyl)imide (PYR$_{14}$-TFSI). Upon electrolyte comparison, EMIMBF$_4$, EMIMOtf, and Na$_2$SO$_4$ electrolytes are most likely to yield the best results with embodiments of the disclosed composite electrodes.

(e) Supercapacitor Performance:

Values of specific capacitance ($C_{sp}$), areal capacitance ($C_A$), volumetric capacitance ($C_v$), coulombic efficiency ($\eta$), peak energy density ($E_v$), and power density (P) were calculated from CV and GCD measurements on two electrode supercapacitors composed of electrodes on CCCF substrates and a paper separator, where the electrode composition, carbon nanotube orientation, and electrolyte are each varied. These calculations are presented in Tables 1 and 2, below. Corresponding plots are presented in FIGS. 13A-13B and 14A-14F.

Figure 13A:
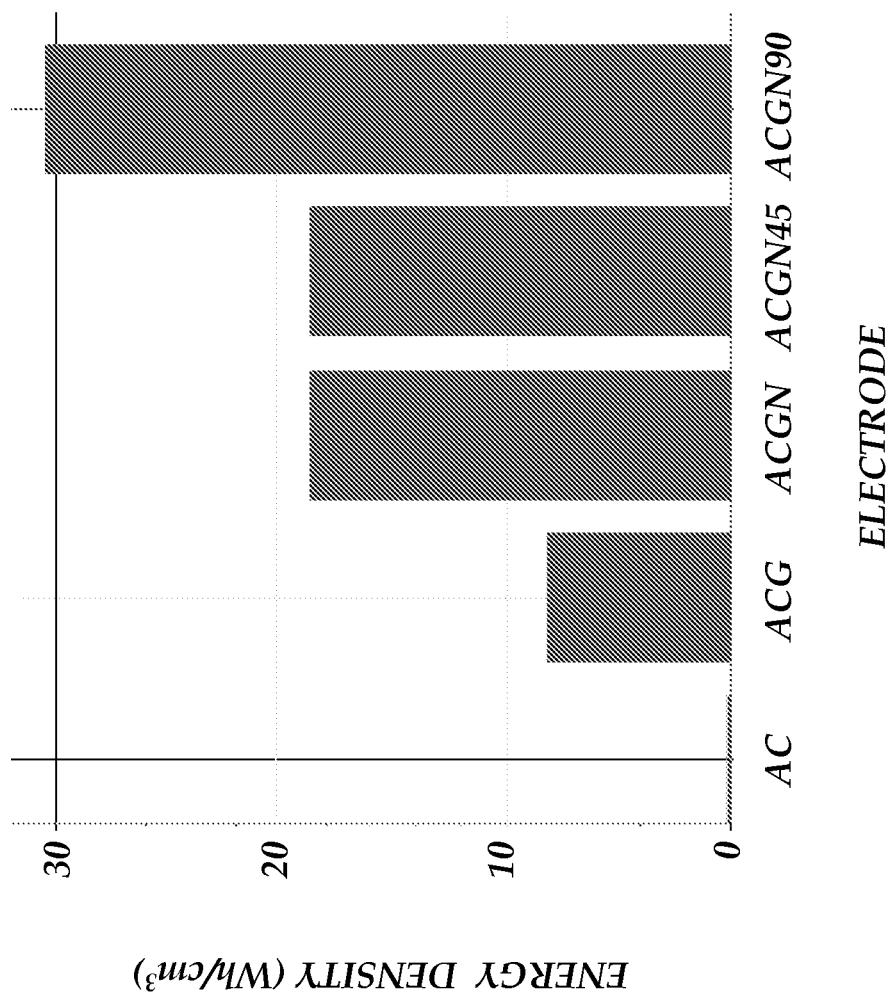
FIG. 13A is a bar chart of energy density (E$_v$) calculated from GCD measurements of embodiments of supercapacitors composed of AC, ACG, ACGN, ACGN45, and ACGN90 electrodes on carbon coated copper substrates and a paper separator using EMIMBF$_4$ as the electrolyte.

FIG. 13A is a bar chart presenting energy density calculated from GCD measurements on supercapacitors composed of AC, ACG, ACGN, ACGN45, and ACGN90 electrodes on CCCF substrates and a filter paper separator using $EMIMBF_4$ as the electrolyte.

Figure 13B:
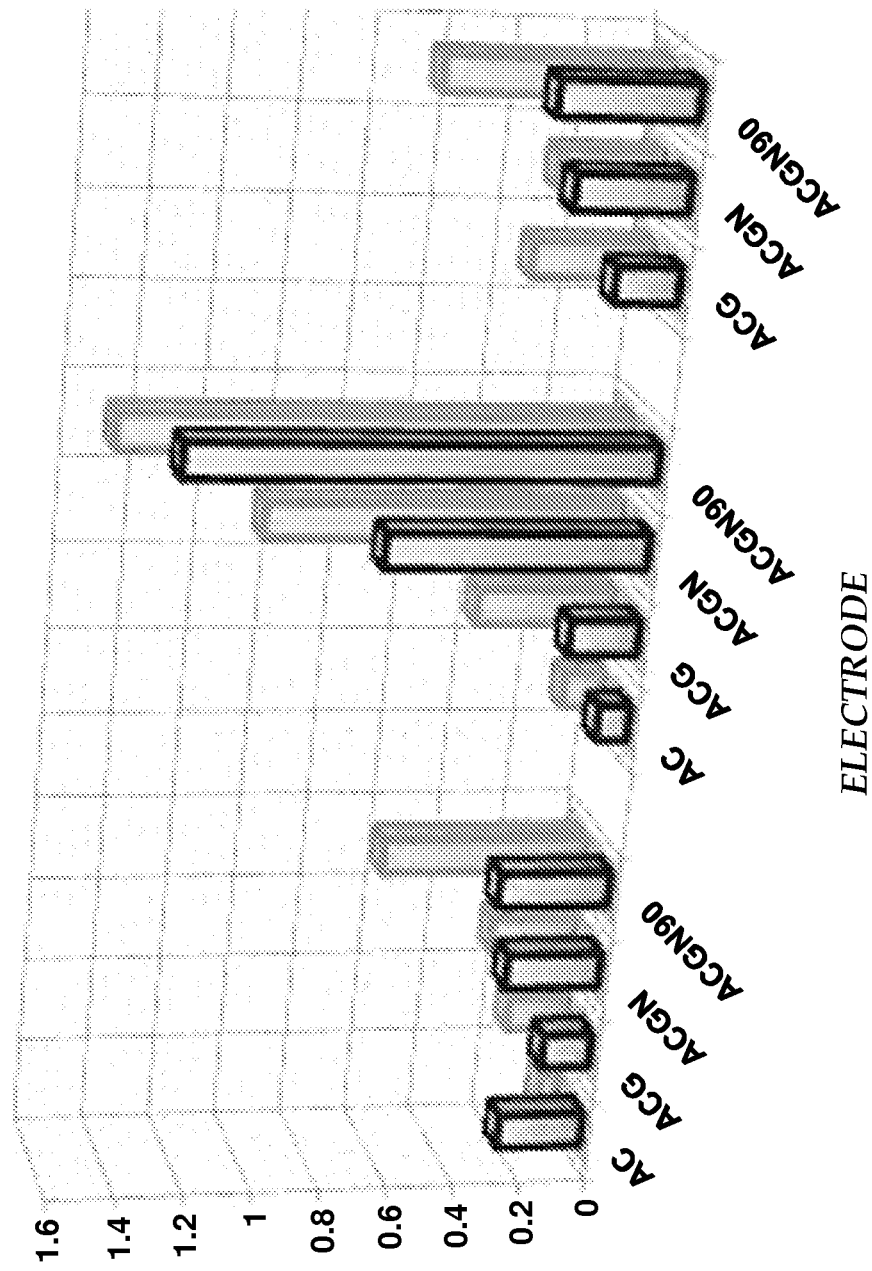
FIG. 13B is a bar chart of specific capacitance (C$_{sp}$) calculated from CV and GCD measurements on embodiments of supercapacitors composed of AC, ACG, ACGN, and ACGN90 electrodes on carbon coated copper substrate and a paper separator using EMIMBF$_4$, H$_2$SO$_4$, or EMIMOtf as the electrolyte.

FIG. 13B is a bar chart presenting specific capacitance calculated from CV and GCD measurements for supercapacitors composed of AC, ACG, ACGN, and ACGN90 electrodes on CCCF substrates and a filter separator using $EMIMBF_4$, $H_2SO_4$, or EMIMOtf as the electrolyte.

Figure 14A:
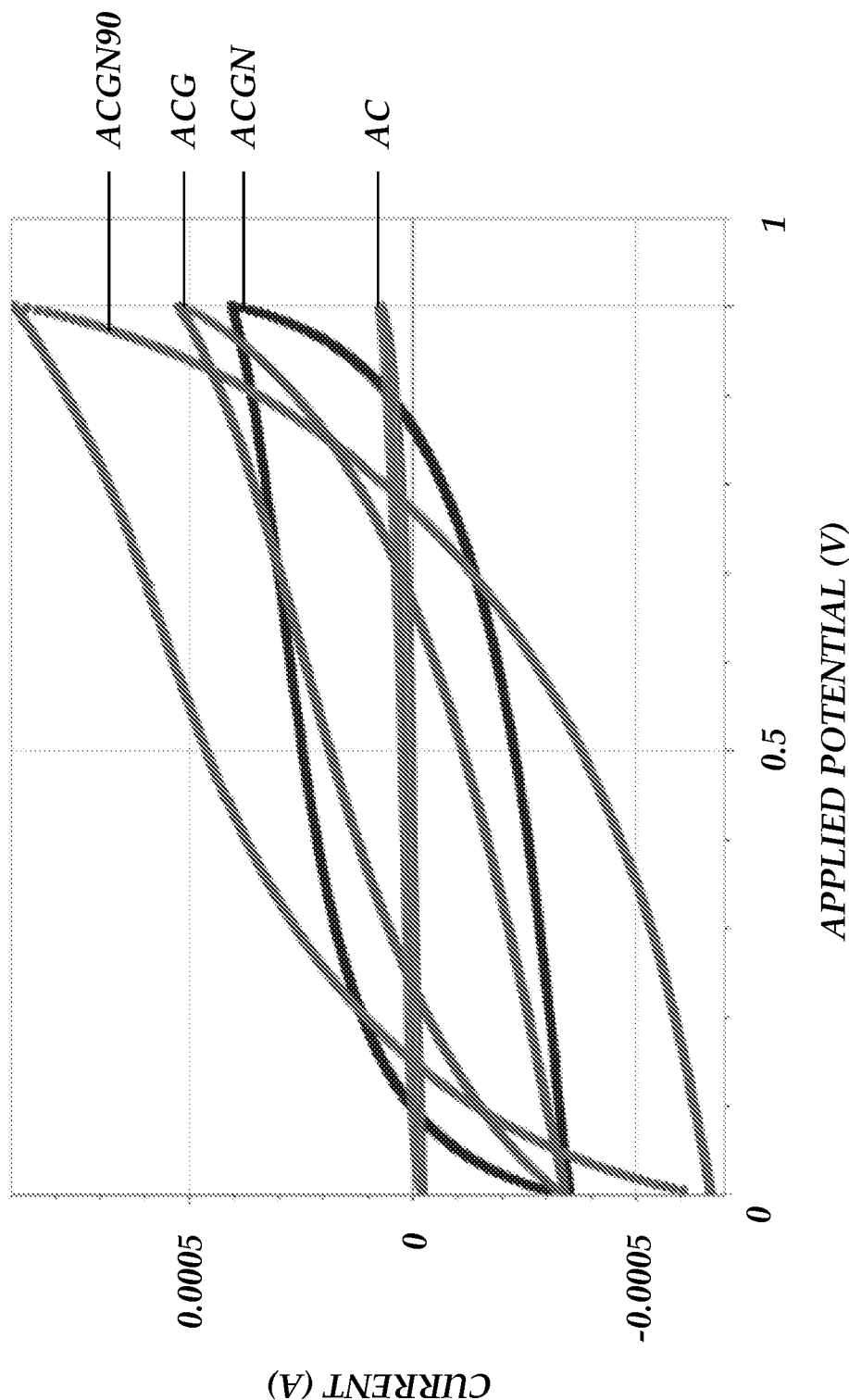
FIGS. 14A-14B are plots of CV (scan rate=0.01 V/s) and GCD (current=0.2 mA) measurements, respectively, on embodiments of supercapacitors composed of AC, ACG, ACGN, and ACGN90 electrodes on carbon coated copper substrates and a paper separator using H$_2$SO$_4$ as the electrolyte.
Figure 14B:
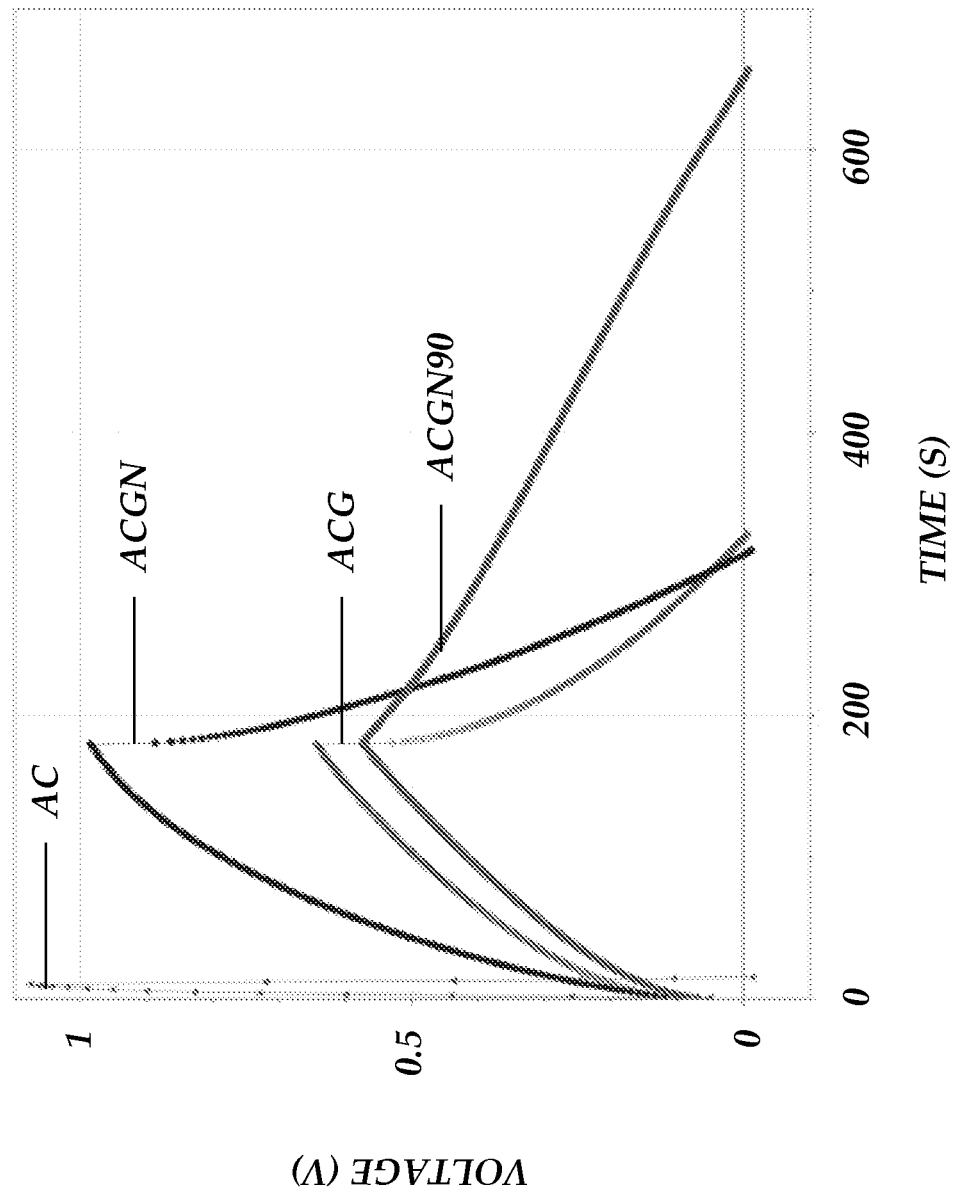

FIGS. 14A-14B presents CV (scan rate=0.01 V/s) and GCD (current=0.2 mA) measurements, respectively, on supercapacitors composed of AC, ACG, ACGN, and ACGN90 electrodes on CCCF substrates and a filter paper separator using $H_2SO_4$ as the electrolyte.

Figure 14C:
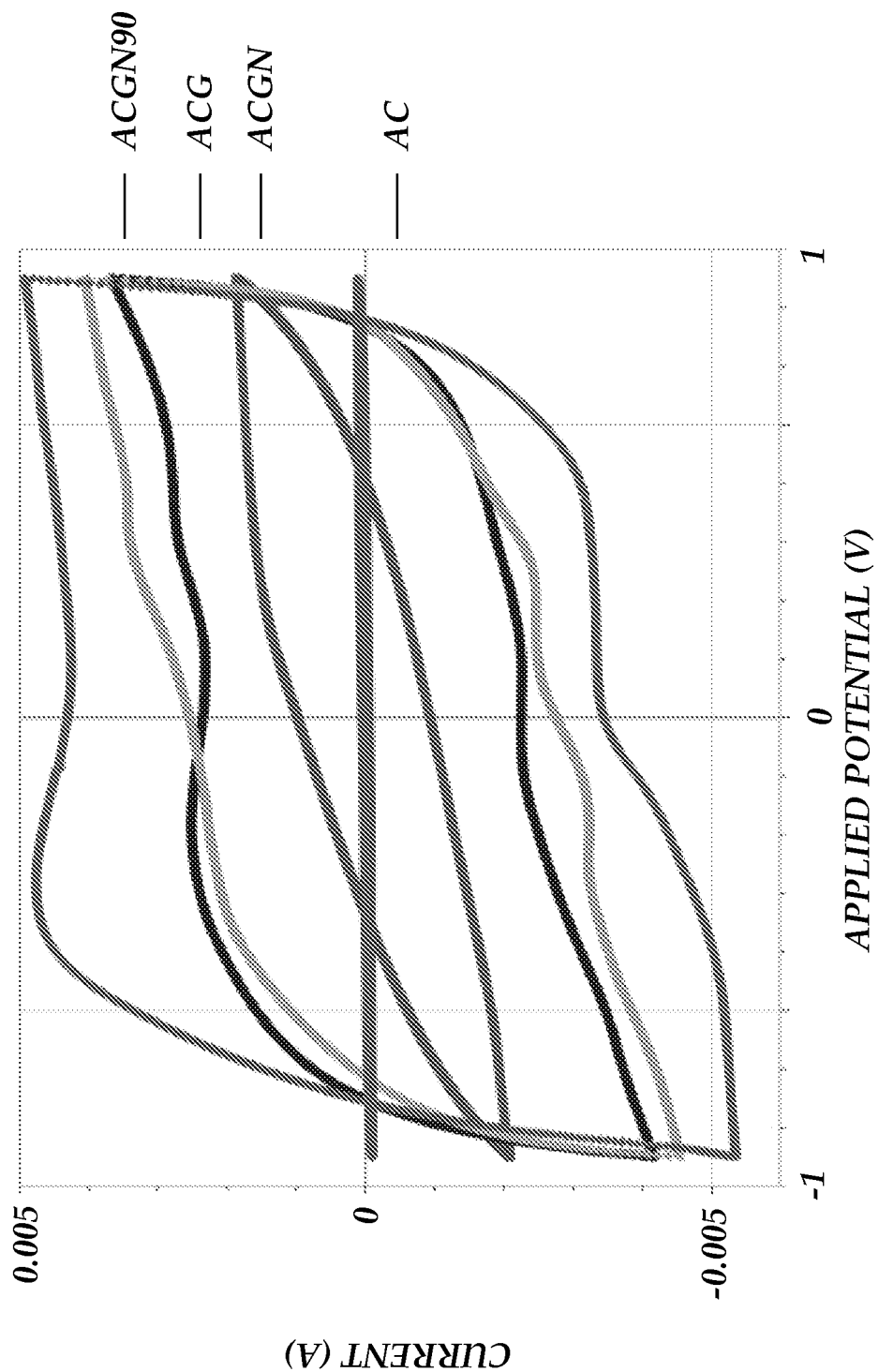
FIGS. 14C-14D are plots of CV (scan rate=0.01 V/s) and GCD (current=0.2 mA) measurements, respectively, on embodiments of supercapacitors composed of AC, ACG, ACGN, and ACGN90 electrodes on carbon coated copper substrates and a paper separator using EMIMBF$_4$ as the electrolyte.
Figure 14D:
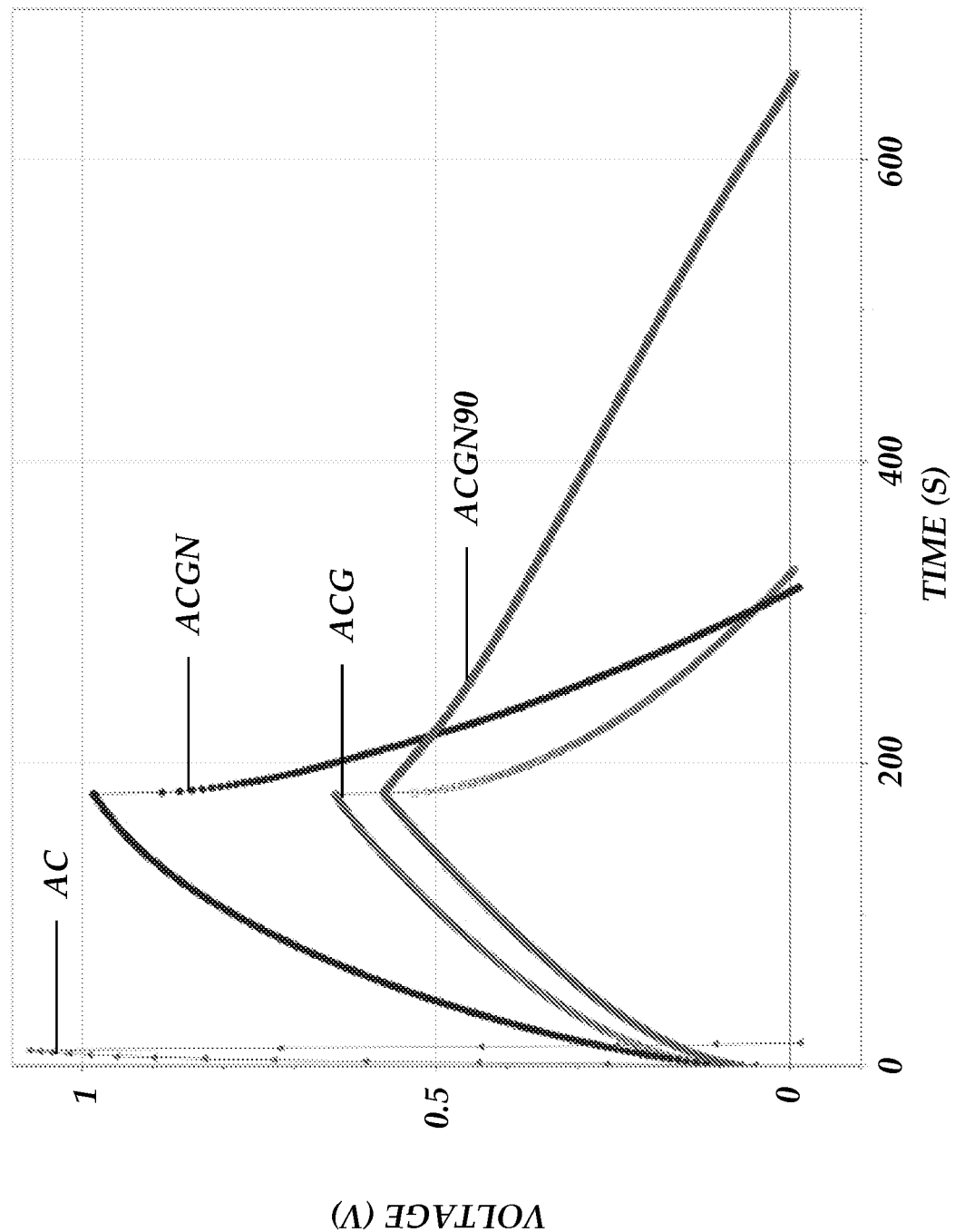

FIGS. 14C-14D presents CV (scan rate=0.01 V/s) and GCD (current=0.2 mA) measurements, respectively, on supercapacitors composed of AC, ACG, ACGN, and ACGN90 electrodes on CCCF substrates and a filter paper separator using $EMIMBF_4$ as the electrolyte.

Figure 14E:
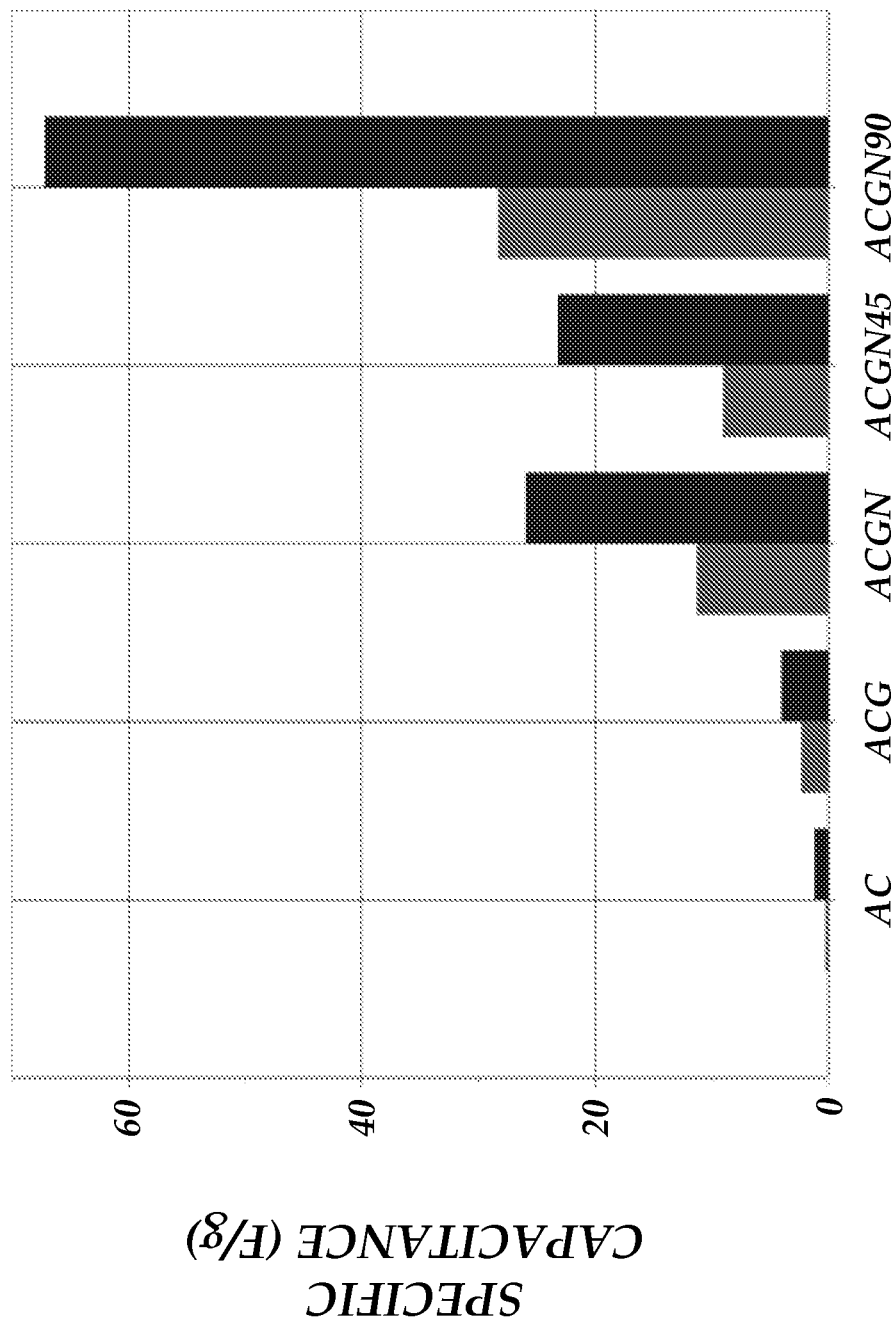
FIGS. 14E-14F are bar charts of specific capacitance and specific areal capacitance, respectively, calculated from CV and GCD measurements on embodiments of supercapacitors composed of AC, ACG, ACGN, ACGN45, and ACGN90 electrodes on carbon coated copper substrates and a paper separator using EMIMBF$_4$ as the electrolyte.
Figure 14F:
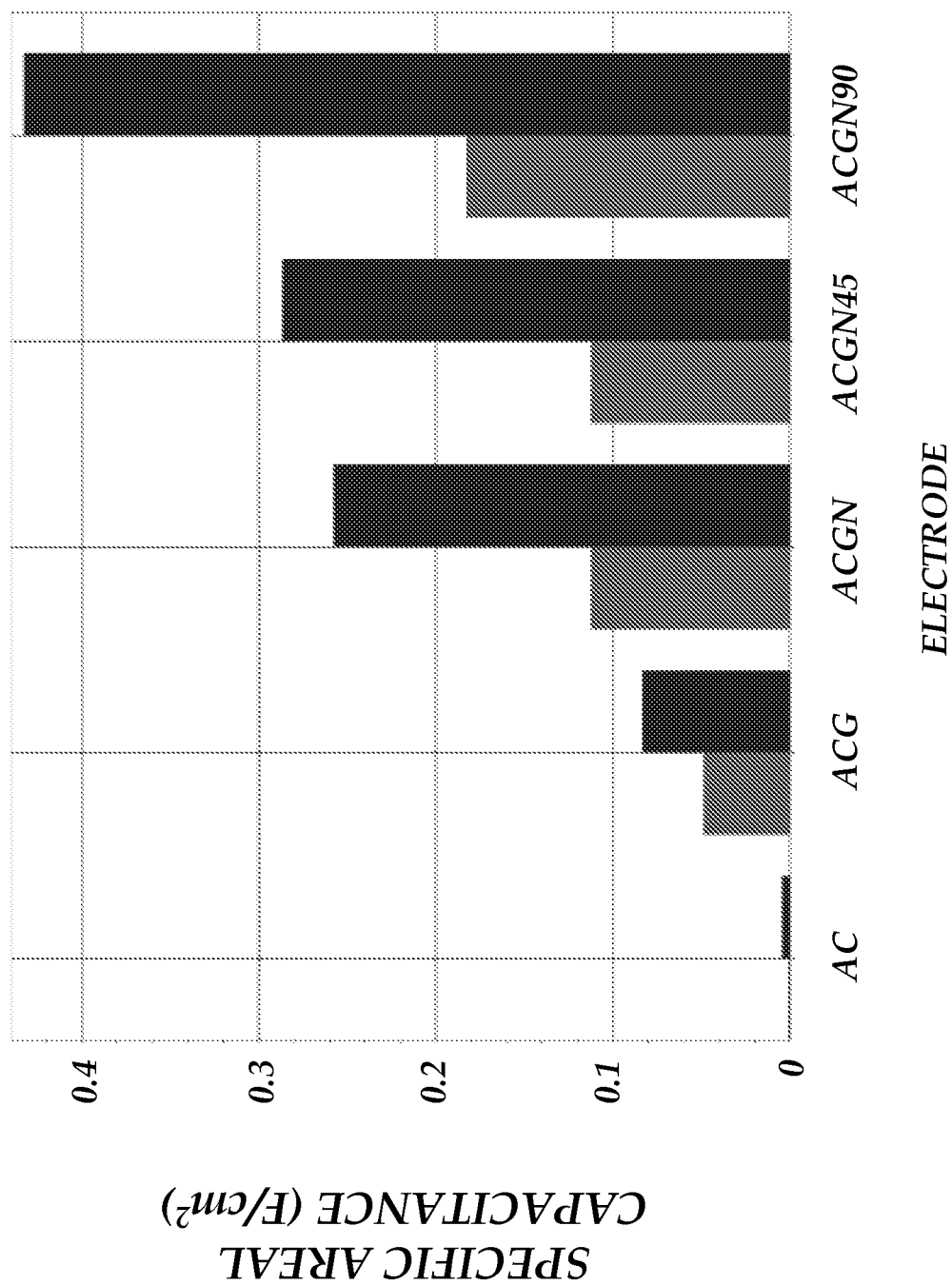

FIGS. 14E-14F present specific capacitance and specific areal capacitance, respectively, calculated from CV and GCD measurements on supercapacitors composed of AC, ACG, ACGN, ACGN45, and ACGN90 electrodes on CCCF substrates and a filter paper separator using $EMIMBF_4$ as the electrolyte.

TABLE 1

| Sample | Test | $C_{sp}$ (F/g) | $C_A$ (F/cm$^2$) | $C_v$ (F/cm$^3$) |
|---|---|---|---|---|
| AC | GCD | 0.285 | 0.00112 | 0.374 |
| ACG | GCD | 2.38 | 0.0491 | 16.4 |
| ACGN | GCD | 11.3 | 0.112 | 37.4 |
| ACGN45 | GCD | 9.07 | 0.112 | 37.4 |
| ACGN90 | GCD | 28.4 | 0.183 | 60.9 |
| AC | CV | 1.2 | 0.00472 | 1.57 |
| ACG | CV | 4.05 | 0.0836 | 27.9 |
| ACGN | CV | 25.9 | 0.258 | 85.9 |
| ACGN45 | CV | 23.2 | 0.287 | 95.6 |
| ACGN90 | CV | 67.1 | 0.433 | 114 |

TABLE 2

| Sample | Test | $\eta$ (%) | $E_v$ (Wh/cm$^3$) | P (W/cm$^3$) |
|---|---|---|---|---|
| AC | GCD | 52.3 | 0.19 | 0.018 |
| ACG | GCD | 90.6 | 8.19 | 0.0205 |
| ACGN | GCD | 82.8 | 18.7 | 0.0156 |
| ACGN45 | GCD | 84.2 | 18.7 | 0.0156 |
| ACGN90 | GCD | 84.2 | 30.5 | 0.0159 |

These results illustrate that each electrolyte exhibits approximately the same trend in capacitance, albeit with different electrolyte dependent amplitude of capacitance values.

Accordingly, further CV data is acquired on supercapacitors including electrodes of AC, ACG, ACGN, and ACGN90 electrodes with CCCF substrate and filter paper separator to better understand the behavior of the electrodes with different electrolytes. FIGS. 15A-15C illustrate CV results for electrolytes of $H_2SO_4$, EMIMTFSi, and $EMIMBF_4$, respectively at scan rates of 0.1 V/s. These data, in combination with that of Tables 1-2 and FIGS. 13A-13B and 14A-14F demonstrate that magnetic field alignment of the carbon nanotubes within the composite electrodes increases the specific capacitance of the supercapacitor. Notably, supercapacitors having electrodes with aligned carbon nanotubes exhibited an increase of about 259% specific capacitance, about 155% specific areal capacitance, about 104% coulomb efficiency, about 263% peak energy density, and about 102% power density as compared to supercapacitors having unaligned electrodes.

(f) Porosity Measurements

To further understand the origins of the observed changes in specific capacitance of the supercapacitor with alignment of the carbon nanotubes and the electrolyte, composite porosity was characterized by ellipsometric porosimetry. This technique measures changes in spectroscopic ellipsometry parameters (e.g., refractive index) as a function of partial pressure in the presence of electrolytes during adsorption and desorption of the electrolytes. From these measurements, the pore size distribution is measured.

FIGS. 16A-16C present normalized pore radius distribution vs. pore radius measured on embodiments of supercapacitors including electrodes of ACGN and ACGN90 with CCCF substrate and filter paper separator with electrolytes of KOH, $EMIMBF_4$, and 1-ethyl-3-methylimidazolium bis (trifluoromethane-sulfonyl)azanide (EMIM-TFSA), respectively. From these measurements, the following conclusions may be drawn:

KOH appears to access the greatest surface area of the examined electrolytes.

Aligned ACGN90 electrodes appear to provide the electrolytes with access to a greater amount of electrode surface area than randomly oriented ACGN electrodes, resulting in the observed increase in the specific capacitance of the supercapacitor.

The terms comprise, include, and/or plural forms of each are open ended and include the listed parts and can include additional parts that are not listed. The term and/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

Statements Regarding Incorporation by Reference and Variations.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition, component or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A composite material, comprising:
a scaffold, comprising: a plurality of graphene sheets each oriented in an independent alignment plane substantially perpendicular to a composite axis; and a plurality of carbon nanotubes, wherein at least a portion of the carbon nanotubes are oriented such that their respective tube axes are oriented substantially at a defined angle with respect to the composite axis; and
a matrix comprising a porous carbon, wherein the scaffold is at least partially embedded in the matrix,
wherein the matrix further comprises an interconnected pore network, extending from an outer surface of the composite to the embedded scaffold, and wherein a mean diameter of pores of the pore network decreases with distance from the outer surface of the composite.

2. The composite of claim 1, further comprising at least two graphene sheets, wherein the plurality of carbon nanotubes extends between the at least two graphene sheets.

3. The composite of claim 2, wherein the at least two graphene sheets are separated by a distance within the range between about 0.8 nm to about 2000 nm.

4. The composite of claim 1, wherein the plurality of graphene sheets comprises at least one of single layer graphene, multi-layer graphene, and reduced graphene oxide (RGO).

5. The composite of claim 1, wherein the plurality of carbon nanotubes are single-walled carbon nanotubes.

6. The composite of claim 1, wherein a mean outer diameter of the plurality of carbon nanotubes is within the range between about 0.8 nm to about 2 nm.

7. The composite of claim 1, wherein a mean length of the plurality of carbon nanotubes is within the range between about 2 nm to about 20 nm.

8. The composite of claim 1, wherein the plurality of carbon nanotubes are functionalized with one or more functional groups selected from the group consisting of carboxylic acid (—COOH), sulphonic acid (—SO$_3$H), amine (—NH$_2$), and hydroxyl (—OH) containing groups.

9. The composite of claim 1, further comprising a binder, wherein the porous carbon is an activated carbon and wherein the binder connects at least a portion of the plurality of graphene sheets to at least a portion of the plurality of carbon nanotubes via the porous carbon matrix.

10. The method of claim 9, wherein the binder is selected from the group consisting of polyvinylidene fluoride (PVDF), polyacrylonitrile (PAN), polytetrafluoroethylene (PTFE), carboxymethylcellulose (CMC), polystyrene, styrene-butadiene rubber (SBR), poly(ethylene oxide), functionalized graphene oxide, and silver paste.

11. The composite of claim 1, wherein the porous carbon is formed from one of carbonized polyacrylonitrile (PAN) and polystyrene.

12. The composite of claim 1, wherein the plurality of graphene sheets and the plurality of carbon nanotubes are mechanically connected to one another.

13. The composite of claim 9, wherein the composite comprises:
about 0.1% to about 5% carbon nanotubes;
about 0.1% to about 5% graphene;
about 70% to about 98.8% porous carbon; and
about 1% to about 20% binder;
on the basis of the total weight of the composite.

14. A composite electrode comprising:
a scaffold, comprising:
a plurality of graphene sheets each oriented in an independently alignment plane substantially perpendicular to a composite axis; and
a plurality of carbon nanotubes, wherein at least a portion of the carbon nanotubes are oriented such that their respective tube axes are oriented substantially at a defined angle with respect to the composite axis;
a matrix comprising a porous carbon, wherein the scaffold is at least partially embedded in the matrix,
wherein the matrix further comprises an interconnected pore network, extending from an outer surface of the composite electrode to the embedded scaffold, and wherein a mean diameter of pores of the pore network decreases with distance from the outer surface of the composite electrode.

15. An electrochemical system, comprising:
a first electrode and a second electrode, wherein at least one of the first electrode and the second electrode is a composite material comprising:
a scaffold, comprising:
a plurality of graphene sheets each oriented in an independent alignment plane substantially perpendicular to a composite axis; and
a plurality of carbon nanotubes, wherein at least a portion of the carbon nanotubes are oriented such that their respective tube axes are oriented substantially at a defined angle with respect to the composite axis;
a matrix comprising a porous carbon, wherein the scaffold is at least partially embedded in the matrix, wherein the matrix further comprises an interconnected pore network, extending from an outer surface of the composite material to the embedded scaffold, and wherein a mean diameter of pores of the pore network decreases with distance from the outer surface of the composite material;
an electrolyte provided between the two electrodes; and
a separator mechanically separating the two electrodes.

16. The electrochemical system of claim 15, wherein the at least one composite electrode is mounted upon a supporting substrate.

17. The electrochemical system of claim 15, wherein the electrolyte is a room-temperature ionic liquid.

18. The electrochemical system of claim 17, wherein the electrolyte is selected from the group consisting of: potassium hydroxide (KOH), sulfuric acid ($H_2SO_4$), 1-butyl-4-methylpyridinium tetrafluoroborate ($4MBPBF_4$), 1-ethyl-3-methylimidazolium trifluoromethanesulfonate (EMIM-OTf), 1-ethyl-3-methylimidazolium tetrafluoroborate ($EMIMBF_4$), sodium sulfate ($Na_2SO_4$), 1-butyl-2,3-dimethylimidazolium bis(trifluoromethylsuphonyl)imide (EMIM-TFSI), N-butyl-N-methylpyrrolidinium bis(trifluoromethanesulfonyl)imide ($PYR_{14}$-TFSI), and 1-ethyl-3-methylimidazolium bis(trifluoromethane-sulfonyl)azanide (EMIM-TFSA).

19. The electrochemical system of claim 15, wherein the electrode further comprises a lithium compound embedded within the composite.

20. The electrochemical system of claim 19, wherein the at least one electrode comprises:
    about 0.1% to about 5% carbon nanotubes;
    about 0.1% to about 5% graphene;
    up to about 2% porous carbon;
    about 88% to about 99.8% lithium compound;
    on the basis of the total weight of the electrode.

21. A method for fabricating a composite material, comprising:
    providing a carbon slurry, the slurry comprising:
        a first solvent;
        a porous carbon;
        a plurality of conductive graphene sheets; and
        a plurality of carbon nanotubes;
    depositing a film of the carbon slurry upon a substrate;
    positioning the carbon slurry film within a magnetic field and sonic wave, wherein the magnetic field lines are oriented at a defined angle with respect to the plane of the substrate and wherein the magnetic field strength is sufficient to induce at least a portion of the carbon nanotubes to orient such that their respective tube axes are substantially parallel to the magnetic field lines; and
    removing at least a portion of the solvents from the deposited film to form a solidified film of the composite,
    whereinafter removing the solvents:
    the plurality of graphene sheets and the plurality of carbon nanotubes form a three-dimensional scaffold at least partially embedded within a matrix formed by the porous carbon,
    the plurality of graphene sheets and the plurality of carbon nanotubes are connected to each other via the porous carbon matrix;
    the plurality of graphene sheets are oriented in an independent alignment plane substantially perpendicular to a composite axis; and
    the plurality of carbon nanotubes are oriented such that their respective tube axes are oriented substantially at a defined angle with respect to the composite axis, wherein the matrix comprises an interconnected pore network, extending from an outer surface of the composite material to the embedded scaffold, and wherein a mean diameter of pores of the pore network decreases with distance from the outer surface of the composite.

22. The method of claim 21, wherein the carbon slurry further comprises a binder and providing the carbon slurry further comprises:
    mixing the porous carbon and the binder with the first solvent to form a first slurry precursor;
    sonicating the first slurry precursor;
    mixing the sonicated first slurry precursor with a dispersion of the plurality of graphene sheets in a second solvent to form a second slurry precursor, wherein the first and second solvents are miscible;
    sonicating the second slurry precursor;
    mixing the sonicated second slurry precursor with a dispersion of the plurality of carbon nanotubes in the first solvent to form the carbon slurry; and
    sonicating the carbon slurry.

23. The method of claim 22, wherein the carbon slurry further comprises a binder and the porous carbon is an activated carbon and wherein the binder connects the plurality of graphene sheets to the plurality of carbon nanotubes via the porous carbon matrix.

24. The method of claim 21, wherein the porous carbon is formed from a polymer precursor resin and providing the carbon slurry further comprises:
    mixing the polymer precursor with the first solvent to form a first slurry precursor;
    sonicating the first slurry precursor;
    mixing the sonicated first slurry precursor with a dispersion of the plurality of graphene sheets in a second solvent to form a second slurry precursor, wherein the first and second solvents are miscible;
    sonicating the second slurry precursor;
    mixing the sonicated second slurry precursor with a dispersion of the plurality of carbon nanotubes in the first solvent to form the carbon slurry; and
    sonicating the carbon slurry.

25. The method of claim 21, wherein the first solvent is selected from the group consisting of: dimethylformamide (DMF) or N-methyl pyrrolidone (NMP) and the second solvent is selected from the group consisting of: N-butyl acetate, acetone, or diethylketone.

26. The method of claim 21, wherein the tube axes of approximately all of the carbon nanotubes are oriented at approximately 90 degrees to the plurality of graphene sheets.

* * * * *